US012802212B2

(12) United States Patent
Cherubini et al.

(10) Patent No.: US 12,802,212 B2
(45) Date of Patent: Nov. 17, 2026

(54) COMPUTER-IMPLEMENTED SYSTEMS AND METHODS FOR OBJECT DETECTION AND CHARACTERIZATION

(71) Applicant: Cosmo Artificial Intelligence—AI Limited, Dublin (IE)

(72) Inventors: Andrea Cherubini, Lainate (IT); Pietro Salvagnini, Padua (IT); Carlo Biffi, Lecco (IT); Nhan Ngo Dinh, Rome (IT)

(73) Assignee: COSMO ARTIFICIAL INTELLIGENCE—AI LIMITED, Dublin (IE)

( * ) Notice: Subject to any disclaimer, the term of this patent is extended or adjusted under 35 U.S.C. 154(b) by 410 days.

(21) Appl. No.: 17/862,353

(22) Filed: Jul. 11, 2022

(65) Prior Publication Data

US 2023/0007982 A1 Jan. 12, 2023

Related U.S. Application Data

(60) Provisional application No. 63/220,585, filed on Jul. 12, 2021.

(30) Foreign Application Priority Data

Jul. 12, 2021 (EP) .................................... 21185179

(51) Int. Cl.
*G06T 7/00* (2017.01)
*A61B 1/00* (2006.01)
(Continued)

(52) U.S. Cl.
CPC ...... *G06T 7/0012* (2013.01); *A61B 1/000096* (2022.02); *G06V 10/255* (2022.01);
(Continued)

(58) Field of Classification Search
CPC .. G06T 7/0012; G06V 10/255; G06V 10/764; A61B 1/000096
See application file for complete search history.

(56) References Cited

U.S. PATENT DOCUMENTS 10,108,850 B1 * 10/2018 Das ........................ G06V 10/82
2018/0253839 A1 * 9/2018 Zur .................. A61B 1/000094
(Continued)

FOREIGN PATENT DOCUMENTS

CN 107230198 A 10/2017

OTHER PUBLICATIONS

Extended European Search Report, issued by European Patent Office in corresponding with European Application No. 21185179.5, mailed Dec. 17, 2021. (10 pages).
(Continued)

*Primary Examiner* — Mohammed H Zuberi

(57) ABSTRACT

A computer-implemented system is provided that receives a real-time video captured from a medical image device during a medical procedure. The real-time video may include a plurality of frames. The system may be adapted to detect an object of interest in the plurality of frames and apply one or more neural networks configured to identify a plurality of characteristics of the detected object of interest, such as classification, size, and/or location. In some embodiments, the system is adapted to identify, based on one or more of the plurality of characteristics, a medical guideline and present, in real-time on a display device during the medical procedure, information for the medical guideline.

29 Claims, 14 Drawing Sheets

(51) Int. Cl.
*G06V 10/20* (2022.01)
*G06V 10/764* (2022.01)

(52) U.S. Cl.
CPC .. *G06V 10/764* (2022.01); *G06T 2207/10068* (2013.01); *G06T 2207/20081* (2013.01); *G06T 2207/20084* (2013.01); *G06T 2207/30028* (2013.01)

(56) References Cited

U.S. PATENT DOCUMENTS

| | | | | |
|---|---|---|---|---|
| 2019/0385018 | A1* | 12/2019 | Ngo Dinh | G06F 18/41 |
| 2020/0337537 | A1 | 10/2020 | Hirasawa et al. | |
| 2020/0387706 | A1* | 12/2020 | Zur | G06T 7/0012 |
| 2021/0073987 | A1* | 3/2021 | Tegzes | G06T 7/11 |
| 2021/0133972 | A1* | 5/2021 | Ngo Dinh | G06N 3/08 |
| 2021/0158511 | A1* | 5/2021 | Guo | G16H 50/30 |
| 2022/0058821 | A1* | 2/2022 | Fu | G06V 10/75 |
| 2022/0284570 | A1* | 9/2022 | Tan | G06N 3/09 |
| 2022/0296081 | A1 | 9/2022 | Nygaard Espeland et al. | |
| 2022/0335599 | A1 | 10/2022 | Hong et al. | |
| 2023/0298306 | A1* | 9/2023 | Baras | G06V 10/74 382/128 |
| 2024/0242351 | A1* | 7/2024 | Kusu | G06T 7/11 |
| 2024/0257946 | A1* | 8/2024 | Prakash | G06T 7/0012 |

OTHER PUBLICATIONS

Michael Byrne et al., “Real-time differentiation of adenomatous and hyperplastic diminutive colorectal polyps during analysis of unaltered videos of standard colonoscopy using a deep learning model,” GUT Microbiota, vol. 68, No. 1, Jan. 1, 2019, pp. 94-100.

Yu Tian et al., “Detecting, Localising and Classifying Polyps from Colonoscopy Videos using Deep Learning,” arxiv.org, Cornell University Library, Jan. 9, 2021 (12 pages).

Majdoubi et al., Estimation of tumor parameters using neural networks for inverse bioheat problem, Elsevier, Computer Methods and Programs in Biomedicine, vol. 205, https://doi.org/10.1016/j.cmpb.2021.106092, dated Jun. 2021, 9 pages.

* cited by examiner

COMPUTER-IMPLEMENTED SYSTEMS AND METHODS FOR OBJECT DETECTION AND CHARACTERIZATION

CROSS-REFERENCE TO RELATED APPLICATION(S)

The present application claims priority to U.S. Provisional Application No. 63/220,585 filed on Jul. 12, 2021 and European Priority Application No. EP21185179.5 filed on Jul. 12, 2021, the entirety of each of the above-referenced applications is hereby incorporated by reference herein.

TECHNICAL FIELD

The present disclosure relates generally to the field of imaging systems and computer-implemented systems and methods for processing real-time video. More specifically, and without limitation, this disclosure relates to systems, methods, and computer-readable media for processing frames of real-time video and performing object detection and characterization. The systems and methods disclosed herein may be used in various applications, such as medical image analysis for polyp detection and characterization, including determining the classification, size, and location of polyps. The systems and methods disclosed herein may also be implemented to provide real-time image processing capabilities, such as identifying, based on one or more of object characteristics, a medical guideline and presenting, in real-time on a display device, information for the medical guideline.

BACKGROUND

Modern vision and image analysis systems require the ability to detect and characterize objects of interest in a scene. An object of interest may be a person, place, feature, or thing. In some applications, such as systems for medical image analysis, the accuracy of object detection and characterization is important to ensure a proper diagnosis and/or treatment. Example objects of interest in medical applications include lesions, polyps and/or other abnormalities on or of human tissue.

Various object detectors and classifiers have been developed, yet many suffer drawbacks. For example, extant systems may lack the capability to detect variations in object types and/or produce false positives. Some also suffer from limited response time or the inability to efficiently process real-time video signals. Still further, extant systems may not provide object characterization capabilities or only limited object information.

Therefore, there is a need for improved image analysis systems, including for medical image analysis. There is also a need for improved object detection and characterization solutions, including systems that can efficiently process real-time video and provide image analysis and object characterization information. Moreover, there is a need for computer-implemented systems and methods that can aggregate data for an object of interest and provide information depending on a given context, including related to the location, size, and/or classification of the object. Such systems and methods would be useful for applications such as polyp detection and characterization, including during an endoscopy or another medical procedure.

SUMMARY

Consistent with some disclosed embodiments, systems, methods, and computer-readable media are provided for processing real-time video, including for processing frames of real-time video and performing object detection and characterization. Embodiments of the present disclosure also relate to systems and methods for object detection and characterization using real-time video from a medical image device. The disclosed embodiments include trained neural networks for detecting objects and determining characterizations of the identified objects, such as classification, location, and/or size. In some embodiments, the trained neural networks are arranged to operate in parallel to more efficiently determine the characterizations of each object during the medical procedure and optionally provide information related to a medical guideline. By way of example, a characterization network may be provided that includes a plurality of trained neural networks, each trained neural network being configured to detect a characterization of an identified object, such as a classification, location, or size. For each identified object, the trained neural networks of the characterization network may be applied and simultaneously operated in parallel to determine the characterizations of the object. As further disclosed herein, object detection and characterization may include polyp detection and characterization, as well as other abnormality detections and characterizations. These and other embodiments, features, and implementations are described herein.

Consistent with the present disclosure, a system of one or more computers can be configured to perform particular operations or actions by virtue of having software, firmware, hardware, or a combination of them installed for the system that in operation causes or cause the system to perform the actions. One or more computer programs can be configured to perform operations or actions by virtue of including instructions that, when executed by data processing apparatus (such as one or more processors), cause the apparatus to perform such operations or actions.

One general aspect includes a computer-implemented system for processing real-time video. The computer-implemented system may include at least one processor configured to receive a real-time video captured from a medical image device during a medical procedure, where the real-time video includes a plurality of frames. The at least one processor may be further configured to detect an object of interest in the plurality of frames and apply one or more neural networks that implement: a trained classification network configured to determine a classification of the object of interest, a trained location network configured to determine a location associated with the object of interest, and a trained size network configured to determine a size associated with the object of interest. Further, the at least one processor may be configured to identify, based on one or more of the classification, the location, and the size of the object of interest, a medical guideline. The at least one processor may be further configured to present, in real-time on a display device during the medical procedure, information for the identified medical guideline. Other embodiments include corresponding computer methods, apparatus, and computer programs recorded on one or more computer storage devices, each configured to perform the above operations or features.

Implementations may include one or more of the following features. The medical procedure may include at least one of an endoscopy, a gastroscopy, a colonoscopy, or an enteroscopy. The object of interest may include at least one of a formation on or of human tissue, a change in human tissue from one type of cell to another type of cell, an absence of human tissue from a location where the human tissue is expected, or a lesion. By way of example, the object of interest may be a polyp. The information for the identified medical guideline may include an instruction to leave or resect the object of interest. The information for the identified medical guideline may also include a type of resection. The at least one processor may be further configured to generate a confidence value associated with the identified medical guideline. The determined classification may be based on at least one of a histological classification, a morphological classification, a structural classification, or a malignancy classification. The determined location associated with the object of interest may be a location in a human body. The location in the human body may be one of a location in a rectum, sigmoid colon, descending colon, transverse colon, ascending colon, or cecum. The determined size associated with the object of interest may be a numeric value or a size classification.

The at least one processor may be further configured to apply one or more neural networks that implement a trained quality network to: determine a frame quality associated with at least one of the plurality of frames, and generate a confidence value associated with the determined frame quality. The at least one processor may be further configured to: aggregate data associated with the determined classification, location, and size when at least one of the determined frame quality or the confidence value is above a predetermined threshold and present, on the display device, at least a portion of the aggregated data. Still further, the at least one processor may be configured to detect a plurality of objects of interest in the plurality of frames and determine a plurality of classifications and sizes associated with the plurality of objects of interest, where a classification and a size in the plurality of classifications and sizes are associated with a detected object of interest in the detected plurality of objects of interest. The at least one processor may be further configured to present, on the display device, information associated with one or more classifications and sizes in the plurality of classifications and sizes. Implementations of these and the other above-described operations and techniques may include hardware, a method or process, or computer software on a computer-accessible medium.

Another general aspect includes a computer-implemented system for processing real-time video. The computer-implemented system may include at least one processor configured to receive a real-time video, where the real-time video includes a plurality of frames collected during a medical procedure. The at least one processor may be further configured to detect an object of interest in the plurality of frames and apply one or more neural networks that implement a trained characterization network configured to: determine a plurality of features associated with the object of interest, and determine confidence values associated with the plurality of features. The at least one processor may be further configured to identify, based on one or more of the plurality of features and the confidence values, a medical guideline and present, in real-time on a display device during the medical procedure, information for the identified medical guideline. Other embodiments include corresponding computer methods, apparatus, and computer programs recorded on one or more computer storage devices, each configured to perform the above operations or features.

Implementations of the above computer-implemented system may include one or more of the following features. The medical procedure may include at least one of an endoscopy, a gastroscopy, a colonoscopy, or an enteroscopy. The object of interest may include at least one of a formation on or of human tissue, a change in human tissue from one type of cell to another type of cell, an absence of human tissue from a location where the human tissue is expected, or a lesion. By way of example, the object of interest may be a polyp. The information for the medical guideline may include an instruction to leave or resect the object of interest. The information for the identified medical guideline may also include a type of resection. The at least one processor may be further configured to generate a confidence value associated with the identified medical guideline. The trained characterization network may include: a trained classification network configured to determine a classification associated with the object of interest and to generate a classification confidence value associated with the determined classification, a trained location network configured to determine a location associated with the object of interest and to generate a location confidence value associated with the determined location, and a trained size network configured to determine a size associated with the object of interest and to generate a size confidence value associated with the determined size. The at least one processor may be further configured to present, on the display device, information associated with at least one of the classification, the location, or the size.

The at least one processor may be further configured to: apply one or more neural networks that implement a trained quality network configured to determine a frame quality associated with at least one of the plurality of frames; and generate a confidence value associated with the determined frame quality. The at least one processor may be further configured to aggregate data associated with the plurality of features when at least one of the determined frame quality or the confidence value is above a predetermined threshold and present, on the display device, at least a portion of the aggregated data. The at least one processor may be further configured to detect a plurality of objects of interest in the plurality of frames, determine a plurality of sets of features associated with the plurality of objects of interest, where a set of features in the plurality of sets of features includes characterization and size information associated with a detected object of interest in the plurality of objects of interest, and present, on the display device, information associated with one or more sets of features in the plurality of sets of features. Implementations of these and the other above-described operations and techniques may include hardware, a method or process, or computer software on a computer-accessible medium.

Another general aspect includes a computer-implemented system for processing real-time video. The computer-implemented system may include at least one processor configured to detect an object of interest in a plurality of frames received from a medical image device and characterize the object of interest, the characterization including determining a plurality of features associated with the object of interest. The plurality of features may include a location and a size of the object of interest. The at least one processor may be further configured to aggregate, when the object of interest persists over more than one of the plurality of frames, information associated with the determined location and size of the object of interest. The at least one processor may present, on a display device, when the determined location is in a first body region and the determined size is within a first range, the aggregated information for the object of interest and present, on the display device, when the determined location is in a second body region and the determined size is within a second range, information indicating a status of the characterization of the object of interest. Other embodiments include corresponding computer methods, apparatus, and computer programs recorded on one or more computer storage devices, each configured to perform the above operations or features.

Implementations may include one or more of the following features. The at least one processor may be further configured to identify, based on the determined location and size of the object of interest, a medical guideline and present, on the display device, information associated with the identified medical guideline. The plurality of features further may include a classification of the object of interest, the classification being based on at least one of a histological classification, a morphological classification, a structural classification, or a malignancy classification. The determined location associated with the object of interest may be a location in at least one of a rectum, sigmoid colon, descending colon, transverse colon, ascending colon, or cecum. The determined size associated with the object of interest may be a numeric value or a size classification.

The at least one processor may be further configured to detect a plurality of objects of interest in the plurality of frames, characterize the plurality of objects of interest, the characterization including determining a plurality of sets of features associated with the plurality of objects of interest, where a set of features in the plurality of sets of features includes characterization and size information associated with a detected object of interest in the plurality of objects of interest and present, on the display device, information associated with one or more sets of features in the plurality of sets of features. Implementations of these and other above-described operations and techniques may include hardware, a method or process, or computer software on a computer-accessible medium.

Another general aspect includes a computer-implemented method for processing real-time video. The computer-implemented method may include receiving a real-time video captured from a medical image device during a medical procedure, the real-time video may include a plurality of frames. The method further includes detecting an object of interest in the plurality of frames, applying one or more neural networks that implement: a trained classification network configured to determine a classification of the object of interest, a trained location network configured to determine a location associated with the object of interest, and a trained size network configured to determine a size associated with the object of interest. The method also includes identifying, based on one or more of the classification, the location, and the size, a medical guideline and presenting, in real-time on a display device during the medical procedure, information for the identified medical guideline.

Systems and methods consistent with the present disclosure may be implemented using any suitable combination of software, firmware, and hardware. Implementations of the present disclosure may include programs or instructions that are machine constructed and/or programmed specifically for performing functions associated with the disclosed operations or actions. Still further, non-transitory computer-readable storage media may be used that store program instructions, which are executable by at least one processor to perform the steps and/or methods described herein.

It will be understood that the foregoing general description and the following detailed description are exemplary and explanatory only, and are not restrictive of the disclosed embodiments.

BRIEF DESCRIPTION OF THE DRAWINGS

The following drawings which comprise a part of this specification, illustrate several embodiments and, together with the description, serve to explain the principles and features of the disclosed embodiments. In the drawings.

DETAILED DESCRIPTION

Figure 1:
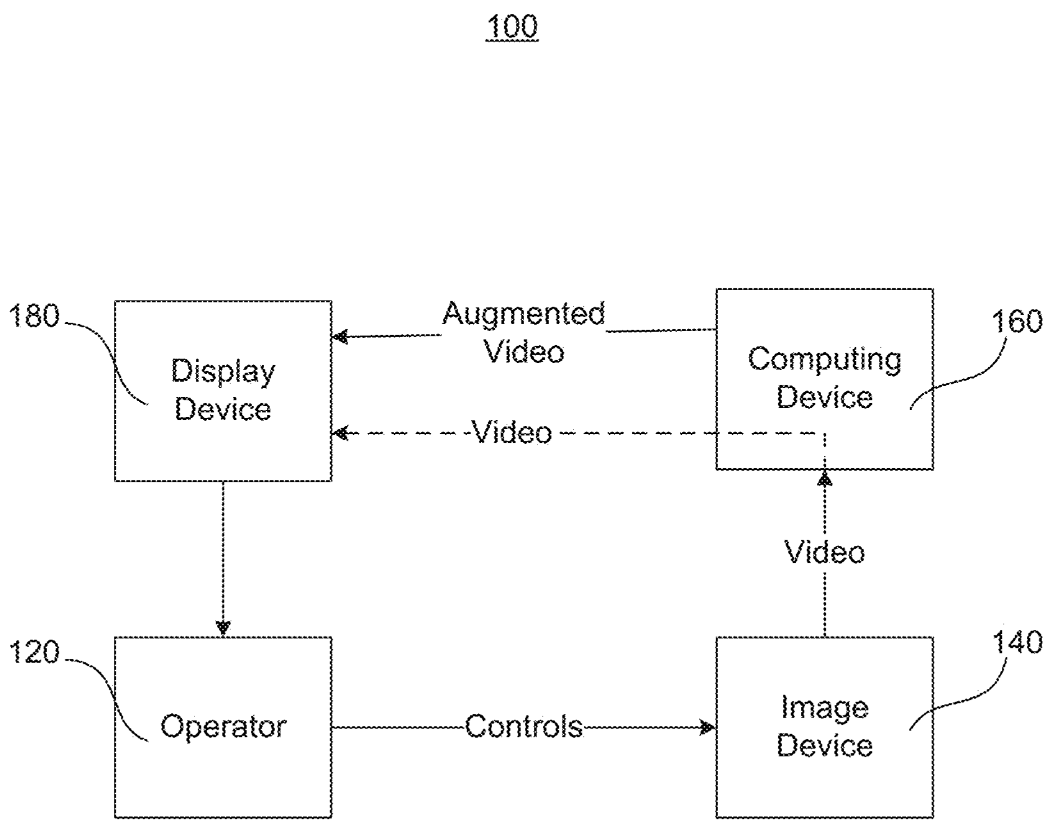
FIG. 1 is a schematic representation of an example computer-implemented system for processing real-time video, consistent with embodiments of the present disclosure.

Exemplary embodiments are described below with reference to the accompanying drawings. The figures are not necessarily drawn to scale. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It should also be noted that as used herein and in the appended claims, the singular forms "a," "an," and "the" include plural references unless the context clearly dictates otherwise.

In the following description, various working examples are provided for illustrative purposes. However, it will be appreciated that the present disclosure may be practiced without one or more of these details.

Throughout this disclosure there are references to "disclosed embodiments," which refer to examples of inventive ideas, concepts, and/or manifestations described herein. Many related and unrelated embodiments are described throughout this disclosure. The fact that some "disclosed embodiments" are described as exhibiting a feature or characteristic does not mean that other disclosed embodiments necessarily share that feature or characteristic.

This disclosure is provided for the convenience of the reader to provide a basic understanding of a few exemplary embodiments and does not wholly define the breadth of the disclosure. This disclosure is not an extensive overview of all contemplated embodiments and is intended to neither identify key or critical elements of all embodiments nor to delineate the scope of any or all aspects. Its purpose is to present some features of one or more embodiments in a simplified form as a prelude to the more detailed description presented later. For convenience, the term "certain embodiments" or "exemplary embodiment" may be used herein to refer to a single embodiment or multiple embodiments of the disclosure.

Embodiments described herein may refer to a non-transitory computer readable medium containing instructions that when executed by at least one processor, cause the at least one processor to perform a method or set of operations. Non-transitory computer readable mediums may be any medium capable of storing data in any memory in a way that may be read by any computing device with a processor to carry out methods or any other instructions stored in the memory. The non-transitory computer readable medium may be implemented as software, firmware, hardware, or any combination thereof. Software may preferably be implemented as an application program tangibly embodied on a program storage unit or computer readable medium consisting of parts, or of certain devices and/or a combination of devices. The application program may be uploaded to, and executed by, a machine comprising any suitable architecture. Preferably, the machine may be implemented on a computer platform having hardware such as one or more central processing units ("CPUs"), a memory, and input/output interfaces. The computer platform may also include an operating system and microinstruction code. The various processes and functions described in this disclosure may be either part of the microinstruction code or part of the application program, or any combination thereof, which may be executed by a CPU, whether or not such a computer or processor is explicitly shown. In addition, various other peripheral units may be connected to the computer platform such as an additional data storage unit and a printing unit. Furthermore, a non-transitory computer readable medium may be any computer readable medium except for a transitory propagating signal.

The memory may include any mechanism for storing electronic data or instructions, including Random Access Memory (RAM), a Read-Only Memory (ROM), a hard disk, an optical disk, a magnetic medium, a flash memory, other permanent, fixed, volatile or non-volatile memory. The memory may include one or more separate storage devices collocated or disbursed, capable of storing data structures, instructions, or any other data. The memory may further include a memory portion containing instructions for the processor to execute. The memory may also be used as a working memory device for the processors or as a temporary storage.

Some embodiments may involve at least one processor. A processor may be any physical device or group of devices having electric circuitry that performs a logic operation on input or inputs. For example, the at least one processor may include one or more integrated circuits (IC), including application-specific integrated circuit (ASIC), microchips, microcontrollers, microprocessors, all or part of a central processing unit (CPU), graphics processing unit (GPU), digital signal processor (DSP), field-programmable gate array (FPGA), server, virtual server, or other circuits suitable for executing instructions or performing logic operations. The instructions executed by at least one processor may, for example, be pre-loaded into a memory integrated with or embedded into the controller or may be stored in a separate memory.

In some embodiments, the at least one processor may include more than one processor. Each processor may have a similar construction, or the processors may be of differing constructions that are electrically connected or disconnected from each other. For example, the processors may be separate circuits or integrated in a single circuit. When more than one processor is used, the processors may be configured to operate independently or collaboratively. The processors may be coupled electrically, magnetically, optically, acoustically, mechanically or by other means that permit them to interact.

Consistent with the present disclosure, disclosed embodiments may involve a network. A network may constitute any type of physical or wireless computer networking arrangement used to exchange data. For example, a network may be the Internet, a private data network, a virtual private network using a public network, a Wi-Fi network, a LAN or WAN network, and/or other suitable connections that may enable information exchange among various components of the system. In some embodiments, a network may include one or more physical links used to exchange data, such as Ethernet, coaxial cables, twisted pair cables, fiber optics, or any other suitable physical medium for exchanging data. A network may also include a public switched telephone network ("PSTN") and/or a wireless cellular network. A network may be a secured network or unsecured network. In other embodiments, one or more components of the system may communicate directly through a dedicated communication network. Direct communications may use any suitable technologies, including, for example, BLUETOOTH™, BLUETOOTH LE™ (BLE), Wi-Fi, near field communications (NFC), or other suitable communication methods that provide a medium for exchanging data and/or information between separate entities.

In some embodiments, machine learning networks or algorithms may be trained using training examples, for example in the cases described below. Some non-limiting examples of such machine learning algorithms may include classification algorithms, data regressions algorithms, image segmentation algorithms, visual detection algorithms (such as object detectors, face detectors, person detectors, motion detectors, edge detectors, etc.), visual recognition algorithms (such as face recognition, person recognition, object recognition, etc.), speech recognition algorithms, mathematical embedding algorithms, natural language processing algorithms, support vector machines, random forests, nearest neighbors algorithms, deep learning algorithms, artificial neural network algorithms, convolutional neural network algorithms, recursive neural network algorithms, linear machine learning models, non-linear machine learning models, ensemble algorithms, and so forth. For example, a trained machine learning network or algorithm may comprise an inference model, such as a predictive model, a classification model, a regression model, a clustering model, a segmentation model, an artificial neural network (such as a deep neural network, a convolutional neural network, a recursive neural network, etc.), a random forest, a support vector machine, and so forth. In some examples, the training examples may include example inputs together with the desired outputs corresponding to the example inputs. Further, in some examples, training machine learning algorithms using the training examples may generate a trained machine learning algorithm, and the trained machine learning algorithm may be used to estimate outputs for inputs not included in the training examples. The training may be supervised or non-supervised, or a combination thereof. In some examples, engineers, scientists, processes and machines that train machine learning algorithms may further use validation examples and/or test examples. For example, validation examples and/or test examples may include example inputs together with the desired outputs corresponding to the example inputs, a trained machine learning algorithm and/or an intermediately trained machine learning algorithm may be used to estimate outputs for the example inputs of the validation examples and/or test examples, the estimated outputs may be compared to the corresponding desired outputs, and the trained machine learning algorithm and/or the intermediately trained machine learning algorithm may be evaluated based on a result of the comparison. In some examples, a machine learning algorithm may have parameters and hyper parameters, where the hyper parameters are set manually by a person or automatically by a process external to the machine learning algorithm (such as a hyper parameter search algorithm), and the parameters of the machine learning algorithm are set by the machine learning algorithm according to the training examples. In some implementations, the hyper-parameters are set according to the training examples and the validation examples, and the parameters are set according to the training examples and the selected hyper-parameters. The machine learning networks or algorithms may be further retrained based on any output.

Certain embodiments disclosed herein may include computer-implemented systems for performing operations or methods comprising a series of steps. The computer-implemented systems and methods may be implemented by one or more computing devices, which may include one or more processors as described herein, configured to process real-time video. The computing device may be one or more computers or any other devices capable of processing data. Such computing devices may include a display such as an LED display, augmented reality (AR), or virtual reality (VR) display. However, the computing device may also be implemented in a computing system that includes a back end component (e.g., as a data server), or that includes a middleware component (e.g., an application server), or that includes a front end component (e.g., a user device having a graphical user interface or a Web browser through which a user can interact with an implementation of the systems and techniques described here), or any combination of such back end, middleware, or front end components. The components of the system and/or the computing device can be interconnected by any form or medium of digital data communication (e.g., a communication network). Examples of communication networks include a local area network ("LAN"), a wide area network ("WAN"), and the Internet. The computing device can include clients and servers. A client and server are generally remote from each other and typically interact through a communication network. The relationship of client and server arises by virtue of computer programs running on the respective computers and having a client-server relationship to each other.

FIG. 1 illustrates an example computer-implemented system 100 for processing real-time video, according to embodiments of the present disclosure. As shown in FIG. 1, system 100 includes an image device 140 and an operator 120 who operates and controls image device 140 through control signals sent from operator 120 to image device 140. By way of example, in embodiments where the video feed comprises a medical video, operator 120 may be a physician or other health care professional. Image device 140 may comprise a medical imaging device, such as an endoscopy imaging device, an X-ray machine, a computed tomography (CT) machine, a magnetic resonance imaging (MRI) machine, or other medical imaging device that produces videos or one or more images of a human body or a portion thereof. Operator 120 may control image device 140 by controlling, among other things, a capture rate of image device 140 and/or a movement or navigation of image device 140, e.g., through or relative to the human body of a patient or individual. In some embodiments, image device 140 may comprise a swallowable capsule device or other form of capsule endoscopy device as opposed to a conventional endoscopy imaging device inserted through a cavity of the human body.

In the example of FIG. 1, image device 140 may transmit the captured video as a plurality of image frames to a computing device 160. Computing device 160 may comprise one or more processors to process the video, as described herein (see, e.g., FIG. 2). In some embodiments, the one or more of the processors may be implemented as separate component(s) (not shown) that are not part of computing device 160 but in network communication therewith. In some embodiments, the one or more processors of computing device 160 may implement one or more networks, such as trained neural networks. Examples of neural networks include an object detection network, a classification detection network, a location detection network, a size detection network, or a frame quality detection network, as further described herein. Computing device 160 may receive and process the plurality of image frames from image device 140. In some embodiments, control or information signals may be exchanged between computing device 160 and operator 120 for purposes for controlling or instructing the creation one or more augmented videos. These control or information signals may be communicated as data through image device 140 or directly from operator 120 to computing device 160. Examples of control and information signals include signals for controlling components of computing device 160, such as an object detection network, a classification detection network, a location detection network, a size detection network, or a frame quality detection network, as described herein.

In the example of FIG. 1, computing device 160 may process and augment the video received from image device 140 and then transmit the augmented video to a display device 180. In some embodiments, the video augmentation or modification may comprise providing one or more overlays, alphanumeric characters, shapes, diagrams, images, animated images, or any other suitable graphical representation in or with the video frames. The video augmentation may provide information related to an object of interest, such as classification, size and/or location information. Additionally, or alternatively, the video augmentation may provide information related to a medical guideline. Information related to a medical guideline may be displayed separately and/or in proximity to the object of interest in the video and contemporaneous with other information related to the object of interest, such as classification, size and/or location. As depicted in FIG. 1, computing device 160 may also be configured to relay the original, non-augmented video from image device 140 directly to display device 180. For example, computing device 160 may perform a direct relay under predetermined conditions, such as when there is no overlay or other augmentation to be generated. In some embodiments, computing device 160 may perform a direct relay if operator 120 transmits a command as part of a control signal to computing device 160 to do so. The commands from operator 120 may be generated by operation of button(s) and/or key(s) included on an operator device and/or an input device (not shown), such as a mouse click, a cursor hover, a mouseover, a button press, a keyboard input, a voice command, an interaction performed in virtual or augmented reality, or any other input.

To augment the video, computing device 160 may process the video from image device 140 and create a modified video stream to send to display device 180. The modified video may comprise the original image frames with the augmenting information to be displayed to the operator via display device 180. Display device 180 may comprise any suitable display or similar hardware for displaying the video or modified video, such as an LCD, LED, or OLED display, an augmented reality display, or a virtual reality display.

Figure 2:
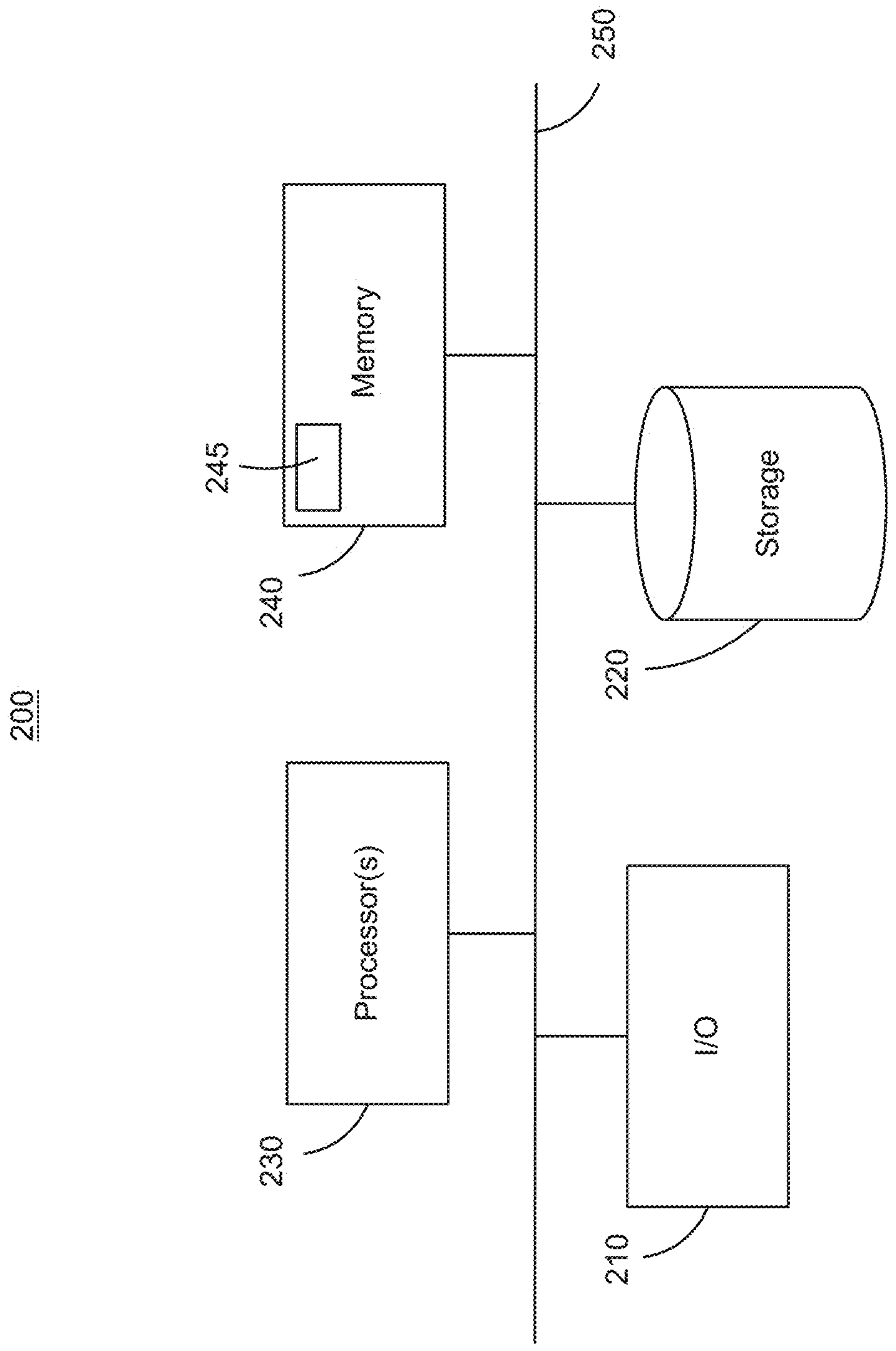
FIG. 2 is a block diagram of an example computing device which may be employed in connection with the example system of FIG. 1 and other embodiments of the present disclosure.

FIG. 2 is a block diagram of an example computing device 200 for processing real-time video, consistent with embodiments of the present disclosure. Computing device 200 may be used in connection with the implementation of the example system of FIG. 1 (including, e.g., computing device 160). It is to be understood that in some embodiments the computing device may include multiple sub-systems, such as cloud computing systems, servers, or any other suitable components for receiving and processing real-time video.

As shown in FIG. 2, computing device 200 may include one or more processor(s) 230, which may include, for example, one or more integrated circuits (IC), including application-specific integrated circuit (ASIC), microchips, microcontrollers, microprocessors, all or part of a central processing unit (CPU), graphics processing unit (GPU), digital signal processor (DSP), field-programmable gate array (FPGA), server, virtual server, or other circuits suitable for executing instructions or performing logic operations, as noted above. In some embodiments, processor(s) 230 may include, or may be a component of, a larger processing unit implemented with one or more processors. The one or more processors 230 may be implemented with any combination of general-purpose microprocessors, microcontrollers, digital signal processors (DSPs), field programmable gate array (FPGAs), programmable logic devices (PLDs), controllers, state machines, gated logic, discrete hardware components, dedicated hardware finite state machines, or any other suitable entities that can perform calculations or other manipulations of information.

As further shown in FIG. 2, processor(s) 230 may be communicatively connected via a bus or network 250 to a memory 240. Bus or network 250 may be adapted to communicate data and other forms of information. Memory 240 may include a memory portion 245 that contains instructions that when executed by the processor(s) 230, perform the operations and methods described in more detail herein. Memory 240 may also be used as a working memory for processor(s) 230, a temporary storage, and other memory or storage roles, as the case may be. By way example, memory 240 may be a volatile memory such as, but not limited to, random access memory (RAM), or non-volatile memory (NVM), such as, but not limited to, flash memory.

Processor(s) 230 may also be communicatively connected via bus or network 250 to one or more I/O device 210. I/O device 210 may include any type of input and/or output device or periphery device. I/O device 210 may including one or more network interface cards, APIs, data ports, and/or other components for supporting connectivity with processor(s) 230 via network 250.

As further shown in FIG. 2, processor(s) 230 and the other components (210, 240) of computing device 200 may be communicatively connected to a database or storage device 220. Storage device 220 may electronically store data in an organized format, structure, or set of files. Storage device 220 may include a database management system to facilitate data storage and retrieval. While illustrated in FIG. 2 as a single device, it is to be understood that storage device 220 may include multiple devices either collocated or distributed. In some embodiments, storage device 220 may be implemented on a remote network, such as a cloud storage.

Processor(s) 230 and/or memory 240 may also include machine-readable media for storing software or sets of instructions. "Software" as used herein refers broadly to any type of instructions, whether referred to as software, firmware, middleware, microcode, hardware description language, or otherwise. Instructions may include code (e.g., in source code format, binary code format, executable code format, or any other suitable format of code). The instructions, when executed by one or more processors 230, may cause the processor(s) to perform the various operations and functions described in further detail herein.

Implementations of computing device 200 are not limited to the example embodiment shown in FIG. 2. The number and arrangement of components (210, 220, 230, 240) may be modified and rearranged. Further, while not shown in FIG. 2, computing device 200 may be in electronic communication with other network(s), including the Internet, a local area network, a wide area network, a metro area network, and other networks capable of enabling communication between the elements of the computing architecture. Also, computing device 200 may retrieve data or other information described herein from any source, including storage device 220 as well as from network(s) or other database(s). Further, computing device 200 may include one or more machine-learning models used to implement the neural networks described herein, and may retrieve or receive weights or parameters of machine-learning models, training information or training feedback, medical guidelines and/or guideline rules, and/or any other data and information described herein.

Consistent with embodiments of the present disclosure, systems, methods, and computer-readable media are provided for processing real-time video. The systems and methods described herein may be implemented with the aid of at least one processor or non-transitory computer readable medium, such as a CPU, FPGA, ASIC, or any other processing structure(s) or storage medium of the computing device. "Real-time video," as used herein, may refer to video received by the at least one processor, computing device, and/or system without perceptible delay from the video's source (e.g., an image device). For example, the at least one processor may be configured to receive real-time video captured from a medical image device during a medical procedure, consistent with disclosed embodiments. A medical image device may be any device capable of producing videos or one or more images of a human body or a portion thereof, such as an endoscopy device, an X-ray machine, a CT machine, or an MRI machine, as described above. A medical procedure may be any action performed with the intention of determining, detecting, measuring, or diagnosing a patient condition, such as an endoscopy, a gastroscopy, a colonoscopy, or an enteroscopy. In embodiments where the medical procedure is an endoscopic procedure, the medical procedure may be used to identify objects of interest (e.g., lesions or polyps) in a location in the human body. Locations in the human body may be the rectum, sigmoid colon, descending colon, transverse colon, ascending colon, or cecum. It is to be understood, however, that the disclosed systems and methods may be employed in other contexts and applications.

The real-time video may comprise a plurality of frames, consistent with disclosed embodiments. A "frame," as used herein, may refer to any digital representation such as a collection of pixels representing of a scene or field of view in the real-time video. In such embodiments, a pixel may represent a discrete element characterized by a value or intensity in a color space (e.g., based on the RGB, RYB, CMY, CMYK, or YUV color models). A frame may be encoded in any appropriate format, such as Joint Photographic Experts Group (JPEG) format, Graphics Interchange Format (GIF), bitmap format, Scalable Vector Graphics (SVG) format, Encapsulated PostScript (EPS) format, or the like. The term "video" may refer to any digital representation of a scene or area of interest comprised of a plurality of frames in sequence. A video may be encoded in any appropriate format, such as a Moving Picture Experts Group (MPEG) format, a flash video format, an Audio Video Interleave (AVI) format, or any other format. A video, however, need not be encoded, and may more generally include a plurality of frames. The frames may be in any order, including a random order. In some embodiments, a video or plurality of frames may be paired with audio.

The plurality of frames may include representations of an object of interest. An "object of interest," as used herein, may refer to any visual item or feature in the plurality of frames the detection or characterization of which may be desired. For example, an object of interest may be a person, place, entity, feature, area, or any other distinguishable visual item or thing. In embodiments where the plurality of frames comprise images captured from a medical imaging device, for example, an object of interest may include at least one of a formation on or of human tissue, a change in human tissue from one type of cell to another type of cell, an absence of human tissue from a location where the human tissue is expected, or a lesion. Examples of objects of interest in a video captured by an image device may include a polyp (a growth protruding from a gastro-intestinal mucosa), a tumor (a swelling of a part of the body), a bruise (a change from healthy cells to discolored cells), a depression (an absence of human tissue), or an ulcer or abscess (tissue that has suffered damage, i.e., a lesion). Other examples of objects of interest will be apparent from this disclosure.

Although some embodiments are described herein with reference to an object of interest being a polyp, it is to be understood that the disclosed systems and methods are not limited to polyps, but may rather be utilized in other contexts and applications including non-medical applications. A "polyp," as used herein, may refer to growths or lesions of the gastro-intestinal mucosa, and may more generally be used herein to refer to a candidate tissue the detection and characterization of which may be of interest. Polyps may be characterized based on classification, such as based on a histological classification, a morphological classification, a structural classification, or a malignancy classification. For example, polyps may be histologically classified using the Narrow-Band Imaging International Colorectal Endoscopic (NICE) or the Vienna classification. According to the NICE classification system, a polyp may be one of three (3) types, as follows: (Type 1) sessile serrated polyp or hyperplastic polyp; (Type 2) conventional adenoma; and (Type 3) cancer with deep submucosal invasion. According to the Vienna classification, a polyp may be one of five (5) types, as follows: (Category 1) negative for neoplasia/dysplasia; (Category 2) indefinite for neoplasia/dysplasia; (Category 3) non-invasive low grade neoplasia (low grade adenoma/dysplasia); (Category 4) mucosal high grade neoplasia, such as high grade adenoma/dysplasia, non-invasive carcinoma (carcinoma in-situ), or suspicion of invasive carcinoma; and (Category 5) invasive neoplasia, intramucosal carcinoma, submucosal carcinoma, or the like.

A polyp may be morphologically classified using the Paris classification. According to the Paris classification system, a polyp may be one of three (3) general types, as follows: (Type I) elevated or polypoid forms, such as pedunculated, sessile, and broad-based; (Type II) flat or superficial forms, such as flat and elevated, completely flat, and superficially depressed; and (Type III) excavated forms, including excavated and ulcerated. Type I are often referred to as polypoid forms while Types II and III are often referred to as non-polypoid forms. A polyp may also be structurally classified based on its shape or appearance. For example, a polyp may be classified as benign if its surface is smooth or round in appearance, or as non-benign or malignant if its surface includes abnormal growths or is irregular in appearance. A polyp may also be classified based on malignancy. A malignancy may be based on a degree of invasion of a disease, such as cancer invasiveness. A polyp may, for example, be classified as benign when there is a small or no invasion of cancer in or around the polyp, and the polyp may be classified as malignant or cancerous when there is invasion of cancer in or around the polyp. Other classifications will be apparent based on this disclosure and may be selected according to the particular application. Accordingly, the present disclosure is not limited to any particular classification or type of object of interest.

A polyp may also be characterized based on its size. A polyp size may be expressed as a numeric value or a size classification. The size of a polyp may be, for example, expressed using any suitable metric value such as millimeters (mm) although any other metric may be used (e.g., inches). A polyp may thus have a size of 1 mm, 5 mm, 10 mm, and so forth. A polyp size may also be expressed as a classification based on one or more suitable size categories, such as (1) "diminutive" or "small" for polyps having a size less than or equal to 5 mm, (2) "non-diminutive" or "large" for polyps having a size between 6 mm and 9 mm, and (3) "very large" for polyps having a size equal to or greater than 10 mm. As will be appreciated, other values, categories, or labels may be used. Other size representations may be employed depending on the particular application and object of interest.

Figure 3A:
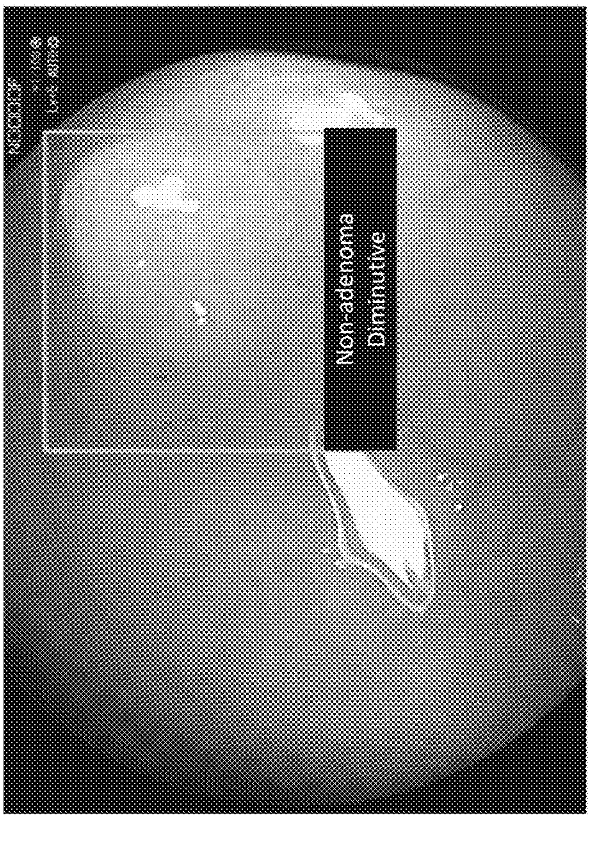
FIGS. 3A and 3B illustrate frame images of example polyps, consistent with embodiments of the present disclosure.
Figure 3B:
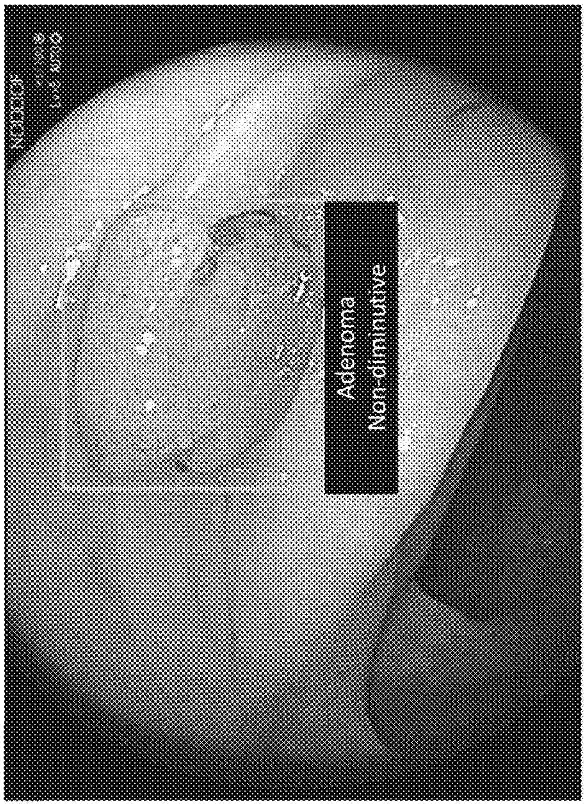

FIGS. 3A and 3B illustrate frame images of example polyps as part of an augmented video display, consistent with embodiments of the present disclosure. As shown, the augmented display (e.g., presented on display device 180) includes a rectangular bounding box surrounding the identified object of interest (i.e., polyp) and information for determined characteristics of the object, such classification, location, and/or size. In the examples of FIGS. 3A and 3B, the illustrated polyps are characterized based on a classification and a size, consistent with the description above. As shown in FIG. 3A, for example, the illustrated polyp is classified as non-adenoma (i.e., not adenomatous) with a diminutive size (i.e., having a size less than or equal to 5 mm). In FIG. 3B. on the other hand, the illustrated polyp is classified as adenoma (i.e., pre-cancerous) with a non-diminutive size (i.e., having a size between 6 mm and 9 mm). Other characterizations, classifications, and size categories may be used, as explained herein. In addition, information related to a medical guideline may be provided as part of the displayed augmented video (see, e.g., FIGS. 5A-5E), as further described below.

The at least one processor of computing device 160 (FIG. 1) may be configured to detect an object of interest in the plurality of frames. An object of interest may be detected based on, for example, a determination of the presence or absence of an object of interest in the plurality of frames of the video. Object detection may be implemented using, for example, one or more machine learning detection networks or algorithms, conventional detection algorithms, or a combination of both. For example, the plurality of frames may be fed to one or more neural networks (e.g., a deep neural network, a convolutional neural network, a recursive neural network, etc.), a random forest, a support vector machine, or any other suitable model, as described above, trained to detect the object of interest. Machine learning detection algorithms, models, or weights may be stored in the computing device and/or system, or they may be fetched from a network or database prior to detection. In some embodiments, a machine learning detection network or algorithm may be re-trained based on one or more of its outputs, such as true/false positive detections or true/false negatives detections. The feedback for re-training may be generated automatically by the system or the computing device, or it may be manually inputted by the operator or another user (e.g., through a mouse or keyboard or other input device). Weights or other parameters of the machine learning detection network or algorithm may be adjusted based on the feedback. In addition, conventional non-machine learning detection algorithms may be used, either alone or in combination with the machine learning detection networks or algorithms.

For example, the presence of the polyps may be detected using one or more machine learning detection networks or algorithms, conventional detection algorithms, or a combination of both, consistent with the disclosed embodiments. The detection of the polyps may include a determined location of the polyp in the frame and be indicated using any suitable graphical representation, which may be overlaid over a frame in which it is detected. In FIGS. 3A and 3B, for example, each illustrated polyp is surrounded by a rectangular bounding box indicating the detection of the illustrated polyps. The detection may be represented using any other graphical representation (e.g., another shape, a color, a pattern, an image, a video, and/or an alphanumeric character) or the detection may not be represented at all as part of the video display.

The at least one processor of computing device 160 may be configured to apply one or more neural networks that implement a trained characterization network configured to determine a plurality of features associated with the object of interest from the plurality of frames, consistent with the disclosed embodiments. The trained characterization network may comprise one or more suitable machine learning networks or algorithms for determining a plurality of features associated with the object of interest, including one or more neural networks (e.g., a deep neural network, a convolutional neural network, a recursive neural network, etc.), a random forest, a support vector machine, or any other suitable model as described above trained to determine features of the object of interest in a plurality of objects of interest. The characterization network may be trained using a plurality of training frames or portions thereof labeled based on the desired features (e.g., classification, size, or location). For example, a first set of training frames (or portions of frames) containing or not containing an object of interest may be labeled as having a feature, and a second set of training frames (or portions of frames) containing or not containing an object of interest may be labeled as not having the feature. Weights or other parameters of the characterization network may be adjusted based on its output with respect to a third, non-labeled set of training frames (or portions of frames) until a convergence or other metric is achieved, and the process may be repeated with additional training frames (or portions thereof) or with live video or frame data, as further described herein.

In some embodiments, the characterization network of computing device 160 may be implemented with a plurality of trained neural networks wherein each trained neural network is adapted to determine a specific characterization or feature of the identified object from the real-time video or frames. For example, the plurality of trained neural networks may include at least one trained neural network to determine the classification of the object, at least one trained neural network to determine the size of the object, and at least one trained neural network to determine the location of the object. As part of computing device 160, each of the trained neural networks may be arranged to operate contemporaneously or in parallel with one another to more efficiently determine characteristics and other information of the object based on the real-time video or frames from image device 140. For example, for each identified object, the trained neural networks of the characterization network may be applied and simultaneously operated in parallel to one another to more efficiently determine the characterizations of the object. Optimizing the arrangement of the trained neural networks also enables computing device 160 to generate the augmented video display, including all determined information related to the detected object, with little or no perceived delay or latency by the clinician or operator viewing the output on display device 180 while performing the medical procedure with image device 140. In some embodiments, the trained neural networks of computing device 160 are also implemented to determine other information, such as a confidence value or medical guideline, as further disclosed herein.

In some embodiments, the trained characterization network of computing device 160 may be configured to determine confidence values associated with the plurality of features. A confidence value for an identified feature may refer to an indication of the level of certainty associated with the identified feature. For example, a confidence value of 0.9 or 90% may indicate that there is a ninety percent certainty that the identified feature is present in an object of interest, while a confidence value of 0.4 or 40% may indicate that there is a forty percent certainty that the identified feature is present, and so forth. Other values, metrics, or representations may be used to represent a confidence value, however, such as alphabetical characters (e.g., "A" for a high confidence value and an "F" for a low confidence value), colors (e.g., green for a high confidence value and red for a low confidence value), shapes (e.g., a check for a high confidence value and a cross for a low confidence value), or any other suitable representation.

The at least one processor of computing device 160 may be configured to apply one or more neural networks to determine a confidence value. In some embodiments, the confidence value associated with an output may be implicitly defined in one hot encoding formulation, where for each possible class a score is output by the network. During training, neural network calibration methods may be used such as mixup and label smoothing to control the range and distribution of confidence values or scores. Alternatively, in other embodiments, a dedicated output node is added to each neural network that provides a confidence estimation and an abstention term can be included in the loss function to train the neural network accordingly. With the extra term in the loss function, the neural network can predict low confidence values when the estimation error is high due to, for example, low quality or cluttered images. In still other embodiments, the neural network is trained to predict both the output and confidence score or label.

In some embodiments, each neural network is trained to obtain in a validation step a correspondence between a threshold value of a confidence score output by the network and the performance of a specific task, such as characterizing an identified object in an input image frame. In the validation stage, an independent and labeled dataset may be used to obtain a correspondence between the thresholds on confidence scores from the neural networks and each specific characterization or feature of the object. Computing device 160 may determine the confidence score threshold for achieving an expected performance level of a neural network performing a specific task of characterizing an identified object. For example, a trained neural network may be discovered to attain a performance sensitivity of 99% when performing a particular task when the confidence score threshold is set to 0.6. Computing device 160 may then execute a neural network to select image frames with an expected performance level of a specific task based on those that satisfy the determined confidence score threshold. Further, computing device 160 may use the desired performance level to implement medical guidelines when using frames from image device 140. One or more metrics may be used for measurement, such as accuracy, precision, recall, sensitivity, npv, specificity, etc. This approach permits the correlation to be obtained between a given threshold on the confidence score output by the neural networks and the expected accuracy of the determined characterization or feature for an identified object.

In some embodiments, the at least one processor of computing device 160 may be configured to apply one or more specific machine learning networks or algorithms trained to detect one or more specific features. For example, the at least one processor may be configured to apply one or more neural networks that implement a trained classification network configured to determine a classification of the object of interest. In some embodiments, the trained classification network may also be configured to generate a classification confidence value associated with the determined classification. The classification may be the same or similar as those described above (e.g., based on at least one of a histological classification, a morphological classification, a structural classification, or a malignancy classification). The classification network may be trained using a plurality of training frames or portions thereof labeled based on one of more classifications. For example, a first set of training frames (or portions of frames) containing or not containing an object of interest may be labeled as "adenoma", and a second set of training frames (or portions of frames) containing or not containing an object of interest may be labeled as "non-adenoma" or another classification (e.g., "serrated"). Other labeling conventions could be used both in binary (e.g. "hyperplastic" vs "non-hyperplastic") and in multiple classes (e.g. "adenoma" vs "sessile serrated" vs "hyperplastic"). Weights or other parameters of the classification network may be adjusted based on its output with respect to a third, non-labeled set of training frames (or portions of frames) until a convergence or other metric is achieved, and the process may be repeated with additional training frames (or portions thereof) or with live data as described herein.

Also, the at least one processor of computing device 160 may be configured to apply one or more neural networks that implement a trained location network configured to determine a location associated with the object of interest. The trained location network may also be configured to generate a location confidence value associated with the determined location. The location may be the same or similar as those described above (e.g., a location in a human body, such as the rectum, sigmoid colon, descending colon, transverse colon, ascending colon, or cecum). The location network may be trained using a plurality of training frames or portions thereof labeled based on one or more locations (e.g., body locations). For example, a first set of training frames (or portions of frames) containing or not containing an object of interest may be labeled as "sigma rectum", and a second set of training frames (or portions of frames) containing or not containing an object of interest may be labeled as "not sigma rectum" or another body location (e.g., "ascending colon"). Weights or other parameters of the location network may be adjusted based on its output with respect to a third, non-labeled set of training frames (or portions of frames) until a convergence or other metric is achieved, and the process may be repeated with additional training frames (or portions thereof) or with live data as described herein.

Furthermore, the at least one processor of computing device 160 may be configured to apply one or more neural networks that implement a trained size network configured to determine a size associated with the object of interest, and in some embodiments the trained classification network may also be configured to generate a size confidence value associated with the determined size. The size may be the same or similar as those described above (e.g., a numeric value or a size classification). The location network may be trained using a plurality of training frames or portions thereof labeled based on size. For example, a first set of training frames (or portions of frames) containing or not containing an object of interest may be labeled as "diminutive" or "small," and a second set of training frames (or portions of frames) containing or not containing an object of interest may be labeled as "non-diminutive" or "not small" or another size value (e.g., "large" or "10 mm"). Weights or other parameters of the location network may be adjusted based on its output with respect to a third, non-labeled set of training frames (or portions of frames) until a convergence or other metric is achieved, and the process may be repeated with additional training frames (or portions thereof) or with live data as described herein.

Consistent with the description above, the trained classification, location, and/or size networks may be stored in the computing device and/or system, or they may be fetched from a network or database prior to characterization. In some embodiments, the trained classification, location, and/or size networks may be re-trained based on one or more outputs, such as true or false feature detections. The feedback for re-training may be generated automatically by the system or the computing device, or it may be manually inputted by the operator or another user (e.g., through a mouse or keyboard or other input device). Weights or other parameters of the trained classification, location, and/or size networks may be adjusted based on the feedback. In some embodiments, conventional non-machine learning detection algorithms may be used, either alone or in combination with the trained classification, location, and/or size networks.

The at least one processor of computing device 160 may be configured to identify, based on one or more of the plurality of features and/or the confidence values, a medical guideline. A "medical guideline," as used herein, may refer to any information provided with the aim of aiding in the determination, diagnosis, or treatment of a patient condition. For example, in embodiments where an object of interest is a polyp or other formation in or on human tissue, the identified medical guideline may include an instruction to leave or resect the object of interest. In some embodiments, when the medical guideline includes an instruction to resect the object of interest, the medical guideline may also include an identification or description of a specific type of resection. For example, the medical guideline may include an instruction to perform Endoscopic Mucosal Resection (EMR) to resect small polyps or precancerous growths, or to perform Endoscopic Submucosal Dissection (ESD) to resect large polyps or likely-cancerous growths, or any other type of resection. Other medical guidelines may be identified based on the specific application or context, however, such as examining the object of interest further, performing other medical examinations, performing an operation, prescribing a drug or medicine, or administrating other treatments. The at least one processor may also be configured to present, in real-time on a display device during capture (e.g., during a medical procedure), information for the identified medical guideline, as described above. The displayed information for the identified medical guideline may be in any suitable representation, such as one or more alphanumeric characters (e.g., the words "leave" or "resect") or abbreviations or text indicating more specifically the type of resection (e.g., "EMR" or "EDS"), shapes (e.g., a check mark or a cross sign), colors (e.g., green or red), images (e.g., an image of a hand or a medical instrument), videos (e.g., a video of a suggested procedure), or any combination thereof. As a further example, in an augmented video display, information related to a medical guideline may be displayed separately and/or in proximity to the object of interest (see, e.g., FIGS. 5A-5E). Additionally, the medical guideline information may be displayed contemporaneous with other information related to the object of interest, such as classification, size and/or location. In cases where there are multiple objects of interest identified in a frame, the medical guideline and other information presented in the augmented video display may be color coordinated such that a unique color is used to display the bounding box, classification information, and/or medical guideline for each identified object. Similar techniques may be used to make the displayed information more quickly discernable or distinguishable to the clinician or operator such as using unique colors for the presented information depending on, e.g., the type of classification and/or urgency of a recommended medical guideline (e.g., green for "non-adenoma" and/or "leave" but red for "adenoma" and/or "resect").

The at least one processor may be configured to generate a confidence value associated with the identified medical guideline. A confidence value for an identified medical guideline may refer to an indication of the level of certainty associated with the identified medical guideline. For example, a confidence value of 0.9 or 90% may indicate that there is a ninety percent certainty that the identified medical guideline is correct, while a confidence value of 0.4 or 40% may indicate that there is a forty percent certainty that the identified medical guideline is correct, and so forth. Other values, metrics, or representations may be used to represent a confidence value, however. For example, a confidence value may be categorized as "high confidence" when the confidence value is above a predetermined threshold (e.g., above 66% confidence), "low confidence" when the confidence value is below a predetermined threshold (e.g., below 33% confidence), or "undetermined" when between two predetermined thresholds (e.g., 33% to 66% confidence). In some embodiments, the at least one processor may also present a confidence score associated with the medical guideline. For example, a confidence score may be represented as alphanumeric characters along with the medical guideline, such as "leave—high confidence" or "resect—30% confidence," although any other suitable representation may be used (e.g., a shape, a color, an image, a video, or a combination thereof).

In some embodiments, the at least one processor of computing device 160 may be configured to apply one or more neural networks to determine a confidence value associated with a medical guideline. For example, as part of or after training the neural networks, a validation stage may be used to associate a confidence value and a medical guideline. In this stage, an independent and labeled dataset may be used to obtain a correspondence between the thresholds on confidence scores from the neural networks and the performance on the task of interest measured according to multiple metrics such as accuracy, precision, recall, sensitivity, npv, specificity, etc. This approach permits the correlation to be obtained between a given threshold on the confidence score output by the neural networks and the expected performance in a real case scenario.

In embodiments where the characterization network determines an object of interest's classification, body location, and/or size, the at least one processor may be configured to identify, based on one or more of the classification, the location, and the size, the medical guideline. For example, in embodiments where the object of interest is a polyp, the medical guideline may be to leave the polyp when it is classified as hyperplastic and to resect the polyp when it is classified as dysplastic or neoplastic. Likewise, the medical guideline may be to leave the polyp when it is determined to be equal to or less than 5 mm or "diminutive" in size and to resect the polyp when it is determined to be greater than 5 mm or "small" or "large" in size. Similarly, the medical guideline may be to leave the polyp when it is determined to be in a non-harmful body location and to resect the polyp when it is determined to be in a harmful body location. In some embodiments, the medical guideline may be determined based on a combination of the classification, the location, and the size. For example, the medical guideline may be to leave the polyp when it is determined to be a hyperplastic polyp located in the sigma rectum having a size that is equal to or less than 5 mm in size. As another example, the medical guideline may be to leave the polyp when it is determined to be a hyperplastic polyp located in the rectum having a "diminutive" size. On the other hand, the medical guideline may be to resect the polyp when it is determined to be an adenoma located in the caecum having a "diminutive" size. Likewise, the medical guideline may be to resect the polyp when it is determined to be an adenoma located in the ascending colon having a "non-diminutive" size. In some embodiments, a confidence value associated with the relevant characterization may be used to determine the medical guideline. For example, the medical guideline may be to resect the polyp only when there is a ninety percent confidence value that the polyp is neoplastic, 10 mm or "large" in size, and/or in a harmful body location, and to leave the polyp otherwise. Confidence values could be expressed also as "high confidence" or "low confidence". Other confidence values and characterizations may be used, however, as described above. The medical guideline determinations disclosed herein are provided for illustrative purposes only and are not intended to be exhaustive, and other medical guidelines will be apparent to those having ordinary skill in the art.

Figure 4A:
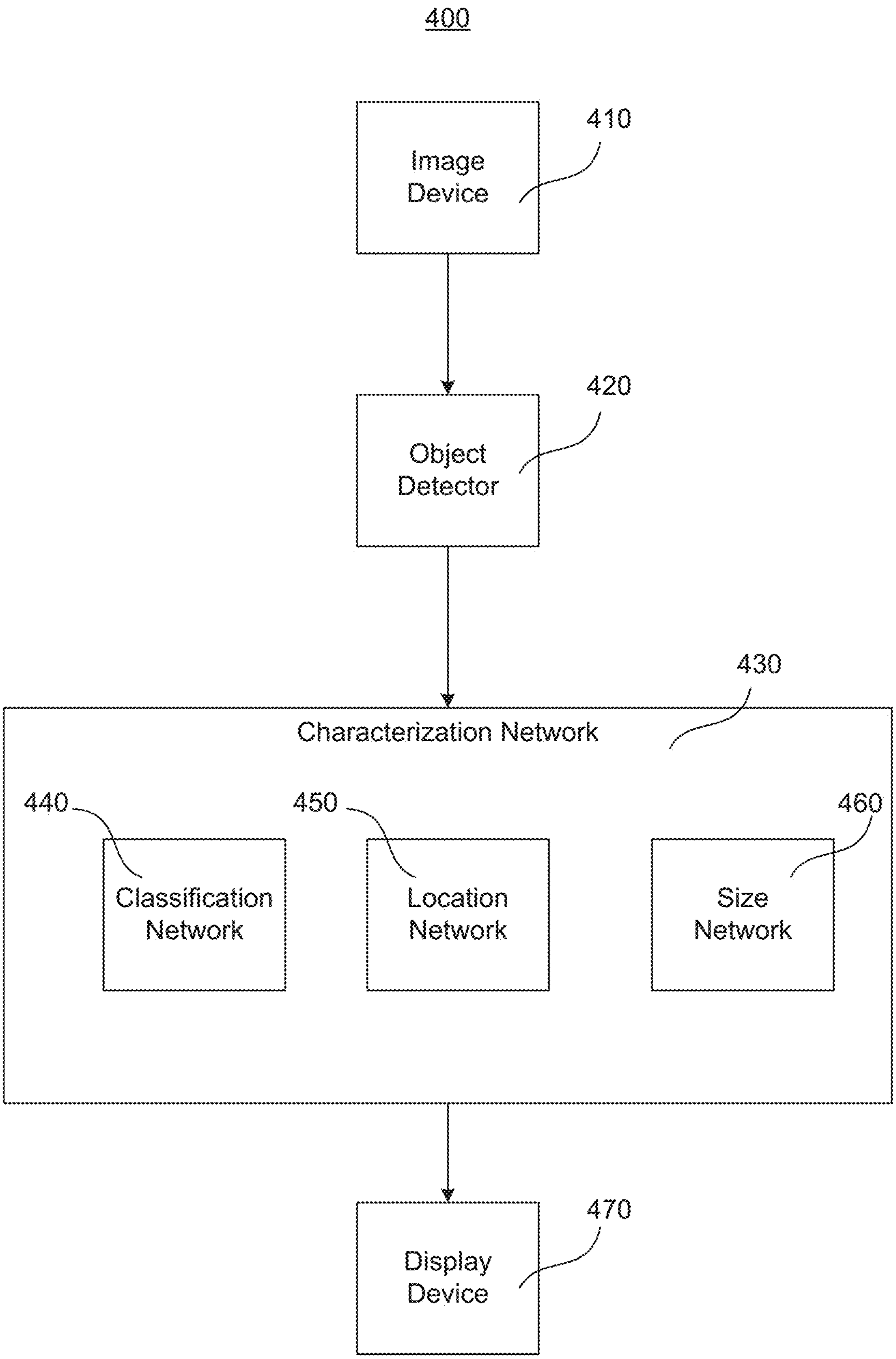
FIG. 4A illustrates an example system for processing real-time video, consistent with embodiments of the present disclosure.

FIG. 4A illustrates an exemplary system of processing real-time video, consistent with embodiments of the present disclosure. As shown in FIG. 4A, a real-time processing system 400 may comprise an image device 410, an object detector 420, a characterization network 430, and a display device 470. Image device 410 may be the same or similar to image device 140 described above in connection with FIG. 1 (e.g., an endoscopy machine, an X-ray machine, a CT machine, an MRI machine, or any other medical imaging device), and display device 470 may be the same or similar as the display device 180 also described above in connection with FIG. 1 (e.g., an LCD, LED, or OLED display, an augmented reality display, a virtual reality display, or the like). Image device 410 may be configured to capture real-time video, which in some embodiments may be captured during a medical procedure (e.g., an endoscopic procedure), as described above. Image device 410 may be configured to feed the captured real-time video to object detector 420.

Object detector 420 may comprise one or more machine learning detection networks or algorithms, conventional detection algorithms, or a combination of both, as described above with respect to the embodiment of FIG. 1 and computing device 160. Object detector 420 may be configured to detect an object of interest, such as a polyp, in frames of the real-time video captured by image device 410. Object detector 420 may also be configured to output a plurality of detections when two or more objects of interest are present in frames of the real-time video. Object detector 420 may be configured to output any detection(s) to characterization network 430.

Characterization network 430 may include one or more trained machine learning algorithms (e.g., one or more neural networks) configured to determine a plurality of features for each object of interest detected by object detector 420, as described above with respect to the embodiment of FIG. 1 and computing device 160. As shown in FIG. 4A, characterization network 430 may include trained machine learning networks or algorithms configured to detect specific features, such as classification network 440 configured to determine a classification of the detected object of interest, location network 450 configured to determine a body location of the detected object of interest, and size network 460 configured to determine a size of the detected object of interest. It is to be understood, however, that characterization network 430 may be modified to include all, some, more, or none of the machine learning networks depicted in FIG. 4A. For example, in some embodiments characterization network 430 may be a single network configured to determine all the features of interest, or characterization network 430 may include machine learning networks to determine features other than classification, location, or size, depending on the specific application or context. Characterization network 430 may also include trained neural networks to determine confidence values and/or medical guidelines, as disclosed herein. Further, characterization network 430 may include one or more processors (similar to computing device 160) to generate an augmented video stream for display to a clinician or operator.

In some embodiments, characterization network 430 may be implemented with a plurality of trained neural networks (e.g., networks 440, 450, and 460 and/or networks for determining confidence values and medical guidelines) that are arranged in operate in parallel with one another to more efficiently determine characteristics and other information related to the identified object from the real-time video or frames. For example, the plurality of trained neural networks may include at least one trained neural network (i.e., classification network 440) to determine the classification of the object, at least one trained neural network (i.e., location network 450) to determine the location of the object, and at least one trained neural network (i.e., size network 460) to determine the size of the object, as well as trained neural networks for determining confidence values and/or medical guidelines. Optimizing the arrangement of trained neural networks (e.g., networks 440, 450, and 460 as well as networks for determining confidence values and medical guidelines) to operate simultaneously in parallel with one another enables all information related to each identified object to be determined efficiently and enables characterization network 430 to generate the augmented video display, including the determined information related to the detected object, with little or no perceived delay by the clinician or operator viewing the augmented video display on display device 470 while performing a medical procedure with image device 410.

In some embodiments, classification network 440, location network 450, and size network 460 may be implemented to provide multiple output values at the same time for each identified object. For example, classification network 440 could be configured to provide as output an optical characterization prediction (e.g., adenoma, hyperplastic, ssl, etc.) as well as a morphology estimation (e.g., sessile, peduncolated, etc.) and a pit-pattern description (Type I, Type II, Type III, . . . ). This may be achieved through a branching in the final layers of the neural network of classification network 440, wherein each branch infers a specific classification. Additionally, or alternatively, multiple instances of networks 440-460 may be instantiated to operate simultaneously in parallel to determine multiple characterizations or features with respect to one or a plurality of detected objects.

For each identified object, classification network 440, location network 450, and size network 460 may be implemented to process the entire frame and/or an image patch around the object of interest. The output of each network 440, 450, and 460 will be one or more predictions for a given class or characteristic or an estimated value (regression) and may include a confidence score, as disclosed above with respect to the FIG. 1 embodiment and computing device 160. Further, each network 440, 450, and 460 could take as input data estimated on the current frame or a buffer of N items from past frames. Optionally, each network could also build an internal representation storing information from the past frames (e.g., a Recurrent Neural Network (RNN) implementation). Training of these neural networks may be based on annotated data with ground truth labels. In some embodiments, the ground truth values may include a confidence or uncertainty value which can be used during training of the neural networks.

In the example of FIG. 4A, characterization network 430 may be configured to identify and output information associated with the determined features and/or related confidence values to display device 470. For example, characterization network 430 may generate an augmented video stream (such as that described herein and with reference to the other figures hereof) for display on display device 470. In some embodiments, characterization network 430 may also be configured to identify and output a medical guideline based on the determined features of each identified object of interest and/or confidence values associated therewith, as described above. Display device 470 may subsequently present, in real-time during capture (e.g., during a medical procedure), information associated with the plurality of features and/or the medical guideline. For example, characterization network 430 may determine and display device 470 may display classification information (e.g., "adenoma" or "non-adenoma", or "hyperplastic" or "non-hyperplastic"), location information (e.g., "rectum" or "caecum"), size information (e.g., "diminutive" or "non-diminutive" or "small" or "large"), and/or a medical guideline (e.g., "leave" or "resect" or "biopsy") for the detected object of interest. In situations where multiple objects of interest are present in the plurality of frames, characterization network 430 may be configured to generate and output characterization and/or medical guideline information for each individual object of interest (e.g., as a feature vector or another suitable data model) and display 470 may consequently display characterization and/or medical guideline information for each individual object of interest (e.g., on or near each object of interest).

Real-time processing system 400 may receive frames of a video from image device 410, process them, and provide in real-time (i.e., simultaneously or approximately at the same time that a physician or operator is performing the medical procedure) an augmented video display with relevant information to an operator of image device 410 for objects of interest identified in the frames. As disclosed herein, characterization network 430 of real-time processing system 400 may be optimized by arranging the trained neural networks (e.g., networks 440, 450, and 460 and/or networks for determining confidence values and medical guidelines) to process frames in parallel (or substantially at the same time) and provide their output more efficiently. With such an arrangement, the augmented video display with all determined information may be presented with little or no perceived delay by the clinician or operator performing the endoscopy or other medical procedure.

In some embodiments, object detector 420 and/or characterization network 430 may run multiple instances of machine learning detection networks in parallel against the plurality of frames of the real-time video from image device 410. Additionally, or alternatively, the frames may be buffered for processing by the trained neural networks. For example, real-time processing system 400 may buffer frames from image device 410 and provide them as input to the neural networks. At each iteration, networks 440-460 may take as input N image frames buffered by system 400. In some embodiments, networks 440-460 process the current frame along with the past N−1 image frames with the output of each network for the current frame also being dependent on the past N−1 frames. With this buffering implementation, real-time processing can be provided with one of three options: (i) there is no output for the first N−1 frames or (ii) the output for the first N−1 frames only depends on the current frame (i.e., there is no buffering in the initial phase) or (iii) the output for the first N−1 frames only depends on the last frame and all the previous ones available. Additionally, there could be other intervals during which one or more of the networks 440-460 are not providing an output. During intervals where there is no output, real-time processing system 400 may communicate the status of the system by causing appropriate messages to be displayed (e.g., status messages such as "processing," "buffering," or "analyzing") via display device 470.

In some embodiments, real-time processing system 400 may determine the number of instances of trained neural networks to run in parallel based on operator input and/or relevant processing parameters (e.g., the frame rate of the video generated by image device 410 and/or a frame buffer size). Real-time processing system 400 may also process only certain frames or areas of interest identified by object detector 420 to include objects. Further, real-time processing system 400 may selectively process frames and regions within the frames based on available system resources and/or performance requirements. Alternatively, or additionally, in other embodiments, real-time processing system 400 may adjust the size of the input object identified by object detector 420 based on a neural network used to determine a characterization. Real-time processing system 400 may adjust identified object size by adjusting the resolution of an image frame or buffer size of image frames with an identified object.

In some embodiments, real-time processing system 400 may control processing based on the number of frames and/or detected objects in the frames. For example, real-time processing system 400 may adjust the processing of frames to keep up with the frame rate of image device 410. In some embodiments, real-time processing system 400 may adjust the buffer size or length in view of the frame rate of image device 410. In some embodiments, real-time processing system 400 may keep up with the frame rate by processing multiple frames in parallel. Real-time processing system 400 may determine the number of neural network instances to run in parallel based on the frame rate of image device 410. Real-time processing system 400 may also determine the number of instances of neural networks 440-460 to run in parallel based on other real-time processing requirements or factors such as processing time delay(s) or restriction(s) due to available system resources (e.g., available hardware and software resources) and accuracy requirements in detecting objects and features of interest of detected objects. Real-time processing system 400 may also achieve real-time processing requirements by adjusting the sampling rate to select a subset of frames from image device 410. Additionally, or alternatively, real-time processing system 400 may sample frames and/or persistent objects detected in the received frames to meet real-time processing requirements.

In some embodiments, real-time processing system 400 may skip execution of one or more trained neural networks depending on operator input or settings (such as a command not to include confidence values and/or medical guidelines and/or command(s) selecting which of the object characterization features to include for processing). The skipping of frames for processing may also be done when there is a lack of an identified object over one or more frames. Additionally, or alternatively, real-time processing system 400 may skip or pause execution of one or more trained neural networks depending on the operating mode of image device 410 (e.g., cleaning versus navigating) and/or the location image device 410 in or relative to a patient's body or organ during the medical procedure. For example, when real-time processing system 400 determines that an endoscope device is out of a patient's colon it may deactivate one or more of the neural networks of the system. Additionally, or alternatively, real-time processing system 400 may skip execution of one or more of the networks 440-460 based on actions on objects or the status of object detector 420. For example, real-time processing system 400 may deactivate the neural networks 440-460 during a resection/surgery of an object identified by object detector 420 or while an operator is performing other tasks (e.g., lesion insufflation) on objects of interest. While one or more networks 440-460 are deactivated, real-time processing system 400 may continue to receive information regarding detected objects and/or features of interest from object detector 420 and/or other system components (e.g., a frame quality network, an object tracker, an aggregator, etc.; see FIG. 6 and the other embodiments disclosed herein).

Although not shown in FIG. 4A, one or more computing devices (such as computing device 160) may be used to implement object detector 420 and characterization network 430. Such computing device(s) may include one or more processors and configured to modify the video from the image device with augmenting information, including the above-described information determined by object detector 420 and characterization network 430. Thus, augmented video may be fed to display 470 for viewing by the operator of image device 410 and other users.

Figure 4B:
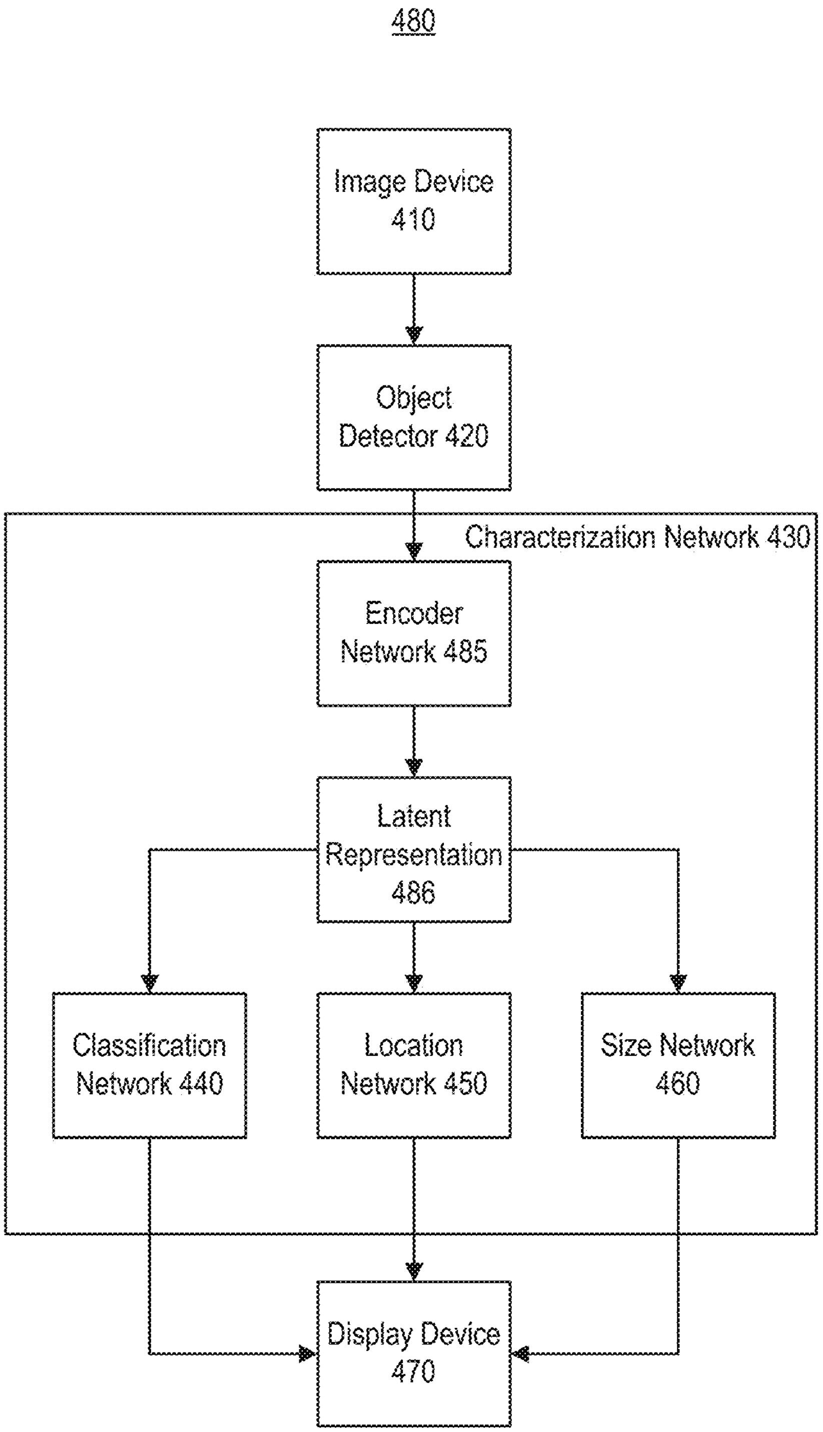
FIGS. 4B-4C illustrate further example systems for processing real-time video, consistent with embodiments of the present disclosure.
Figure 4C:
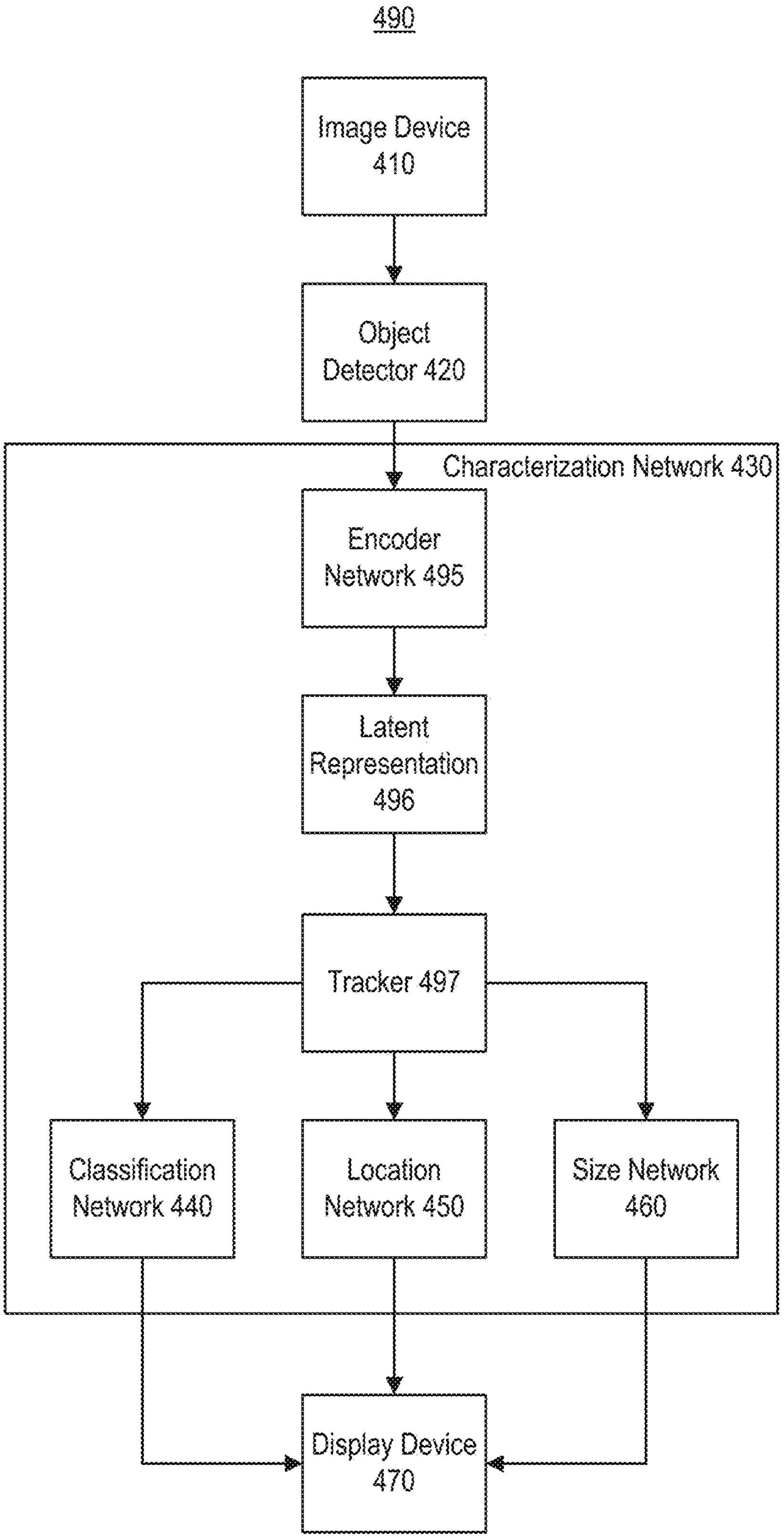

As disclosed herein, the trained neural networks of characterization network 430 may be arranged to operate in parallel to more efficiently determine the characterizations (e.g., classification, location, and size) of identified objects during a medical procedure. Referring now FIGS. 4B and 4C, further arrangements and features are disclosed for optimizing real-time processing, consistent with embodiments of the present disclosure. It will be appreciated that FIGS. 4B and 4C are non-limiting examples and that they may be modified to include other components and features disclosed herein (e.g., a frame quality network (see network 620 of FIG. 6) in combination with characterization network 430). Furthermore, the teachings of FIGS. 4B and 4C may be adapted and/or combined with other teachings herein, such as those of the embodiments described with reference to FIG. 6 and/or the other figures provided herein.

FIG. 4B illustrates another example system for real-time processing, consistent with embodiments of the present disclosure. As illustrated in FIG. 4B, real-time processing system 480 includes an image device 410, object detector 420, and display device 470. These components may be implemented and configured similar to the corresponding components described above for the FIG. 4A embodiment. Further, characterization network 430 may include features similar to that previously described with reference to FIG. 4A, however, in the FIG. 4B embodiment it includes some additional components and optimization features. For example, as illustrated in the drawing, an encoder network 485 and latent representation 486 are provided in combination with the trained neural networks, including classification network 440, location network 405, and size network 460. Object detector 420 may communicate to encoder network 485 objects that are identified in the frames received from image device 410. Encoder network 485 may process entire frames with identified objects and/or a patch area around each object of interest in a frame determined by object detector 420. Additionally, or alternatively, in some embodiments, encoder network 485 may take as input for processing information related to a bounding box or area surrounding the detected object, which may be represented as a list of numbers or a mask. Encoder network 485 may encode input information (e.g., one or more image frames or surrounding areas representing the detected object(s) of interest) and generate a feature vector representing of the input information. Encoder network 485 may include one or more recurrent neural networks and/or long short-term memory neural networks. Encoder network 485 may receive the input information related to the detected object(s) of interest and encode that information by generating a feature vector representation of the detected object(s). After encoding by encoder network 485, latent representation 486 may take as input the feature vector representation and provide as output an embedding representation in latent space. The latent representation 486 reduces data from a high dimension (i.e., the feature vector representation) to a low dimension (i.e., the latent space representation) and provides storage savings and aids in computational efficiency in processing the object data. By way of example, the latent space representation may include an array of N floats, where N represents the number of frames or objects processed by encoder network 485.

Encoder network 485 and latent representation 486 may be implemented with one or more neural networks that are trained using a combination of unsupervised reconstruction loss and a supervised loss based on classification, location, and size tasks. Additionally, or alternatively, encoder network 485 can be trained with a loss from the contrastive loss family such as triplet loss or quadruplet loss which enforces a structured organization of the latent space. In this way, the latent space can assign a similar representation to image frames belonging to the same object and a more robust distance metric can be defined between latent representations. As discussed above, encoder network 485 may embed the inherent structure of the detected object(s) by projecting into a latent space, for example, latent representation 486. Encoder network 485 together with latent representation 486 may process image frame(s) or surrounding area(s) with each detected object to project into latent space by encoding layers of the network resulting in a latent vector in a lower dimension than the detected object(s) in the processed frames or surrounding areas. As discussed above, this provides several benefits including reducing storage requirements and improving processing efficiencies with respect to the object data.

In some embodiments, a tracking module (not shown in FIG. 4B but see tracker 497 in FIG. 4C and the further description thereof) may exploit and benefit from the improved latent representation in associating image frames belonging to the same object. To learn a latent space which is the most effective, multiple losses are combined together and their relative magnitude may be adjusted during training of the neural network(s) of the tracking module. For example, in the first part of the learning, the reconstruction and contrastive loss may have a higher magnitude and serve as a regularization term to prevent overfitting, then the weight of the specific losses for the tasks of interest may be increased later during training to maximize performance on those.

For each object, the embedded representation in latent space (i.e., the output of latent representation 486) may be fed in parallel to the three characterization networks (i.e., classification network 440, location network 405, and size network 460) to determine the characteristics or features for the object. Advantageously, with this implementation, the trained neural networks 440-460 will be small (i.e., just a few fully connected layers) since the encoding part is shared and performed within the encoder network 485. This reduces the overall computational cost and efficiency of the characterization network 430. Consequently, real-time processing system 480 benefits from a reduction in time needed to process and characterize objects of interest and provide output to display device 470.

FIG. 4C illustrates another example system for real-time processing, consistent with embodiments of the present disclosure. Real-time processing system 490 may be similarly constructed with components and features described above for real-time processing system 480 (FIG. 4B), but it further includes a tracker 497 implemented with one or more neural networks that take advantage of temporal information. More specifically, in the embodiment of FIG. 4C, neural networks 440-460 of real-time processing system 490 may be networks that take as input a buffer of consecutive frames of the same object identified by object detector 420. Advantageously, using tracker 497, real-time processing system 490 may leverage temporal information by using Recurrent Neural Networks (RNNs) and/or Long Short-Term Memory (LSTM) neural networks that maintain a memory of the same object detected in past frames by object detector 420. Real-time processing system 490 may keep track of previously identified objects in past frames using tracker 497. In some embodiments, tracker 497 may perform a tracking operation by associating objects detected at the current time in the current set of frames with the objects detected in the previous frames. Tracker 497 may perform this object tracking operation after the computation of latent representation 496 of an object's encoded information so that each detected object's box information is associated with its past history. Tracker 497 may utilize the similarity of latent representation 496 of an object to track the history of that object across current and past frames. Tracker 497 may determine the similarity of latent representation 496 of an object between current and past image frames based on one or more metrics, such as Mean Square Error (MSE), Mean Absolute Error (MAE), etc. As a result of the operation performed by tracker 497, the characterization networks 440-460 may correctly associate objects with their past history in frames and thereby leverage temporal information for each object to more accurately determine features for the object (i.e., classification, location, and size) as well as provide improved confidence values.

Characterization network 430 may aid in determining characteristic features of objects of interest in frames accessed directly from image device 410 or storage (e.g., storage 220 or buffer device with memory) containing previously generated image frames. Characterization network 430 allows inclusion of various networks for simultaneously determining various characteristic features of objects and optimizing the processing of image frames when determining characteristic features.

Characteristic network 430 may be composed of multiple networks and configured to select and unselect various configurations of networks for identifying objects of interest in image frames and determining their characteristics in an optimized manner. Characteristic network 430 may also be configured to have multiple copies of the same network to parallel process image frames or patches of an image frame to determine characteristics. In some embodiments, characteristic network 430 optimizes frame processing by selecting the required networks and configuring the order of networks to pre-process image frames by executing common operations across networks. For example, characterization network 430 may utilize encoder network 485 and latent representation 486 to pre-process images and have smaller networks to determine characteristics in an efficient manner while using less computational resources.

Figure 5A:
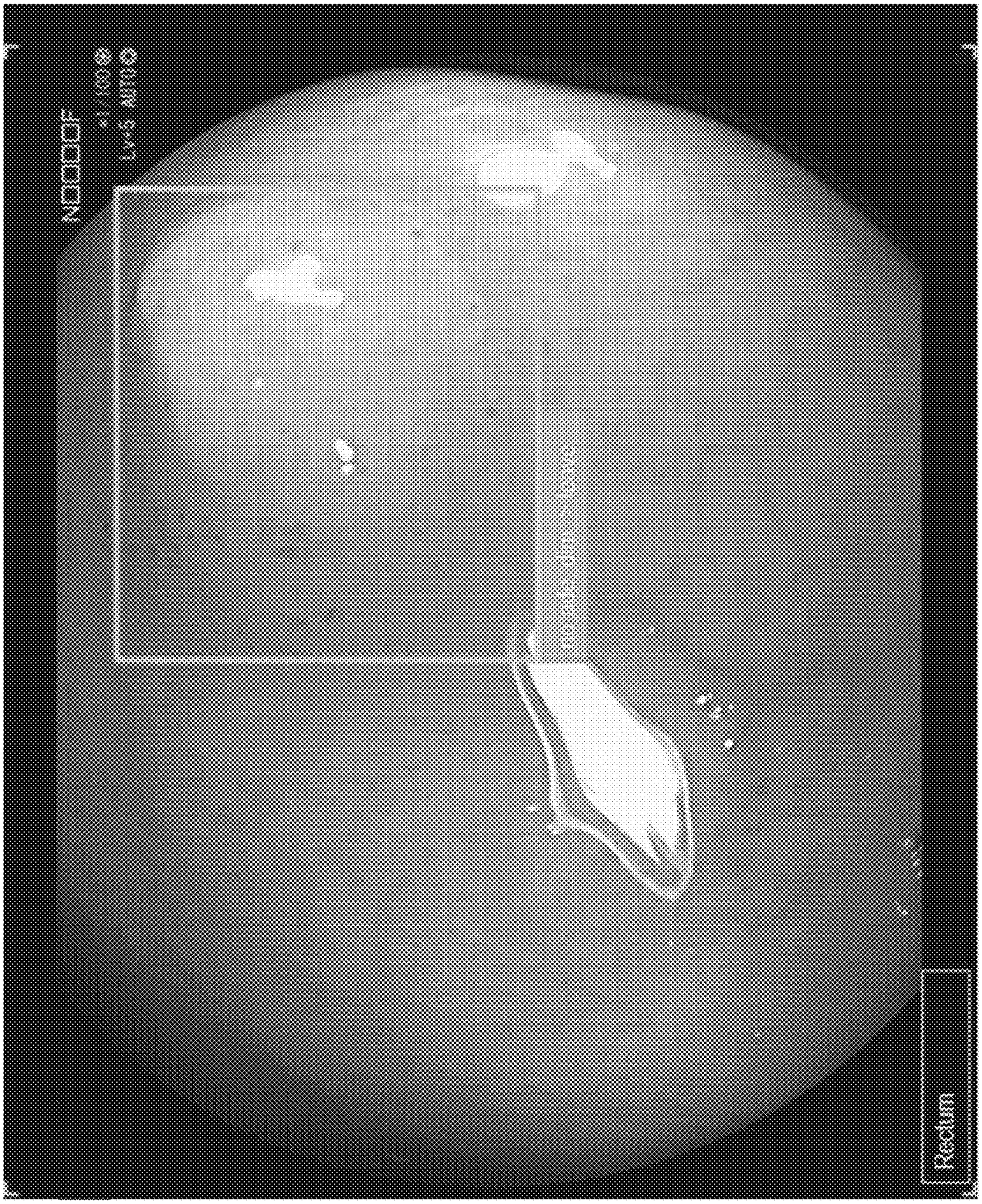
FIGS. 5A-5E illustrate frame images of example augmented frames containing characterization and medical guideline information, consistent with embodiments of the present disclosure.
Figure 5B:
Figure 5C:
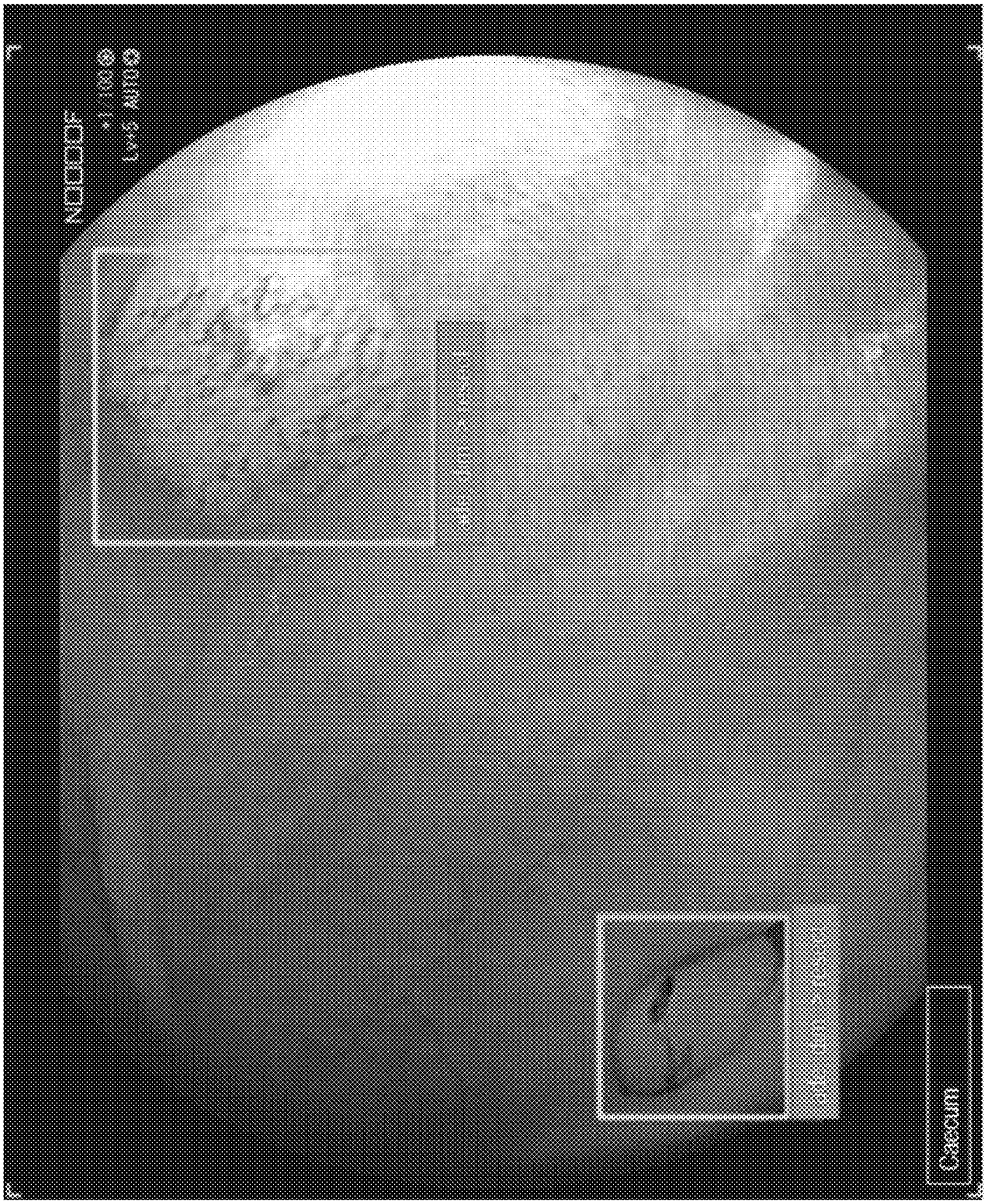
Figure 5D:
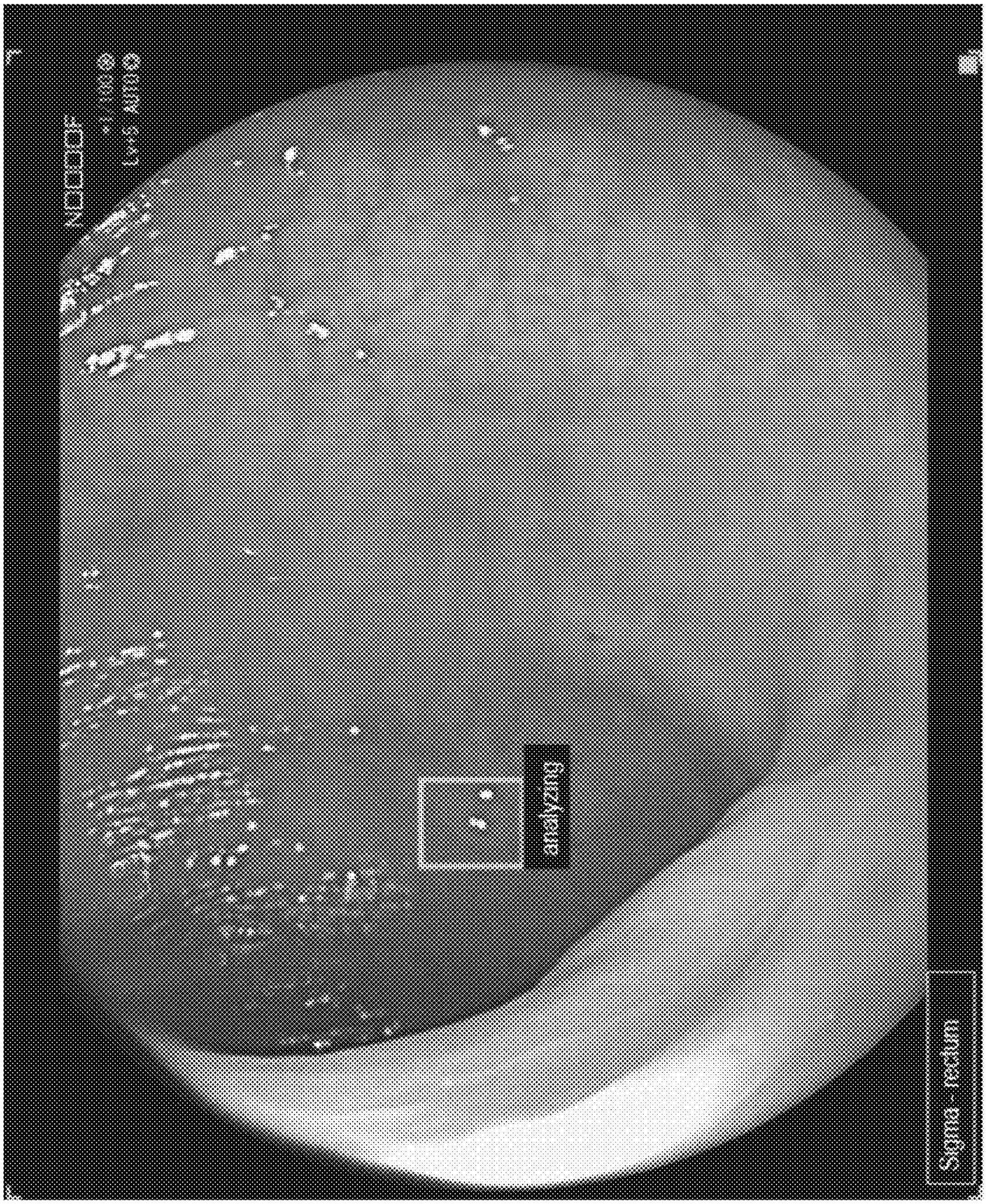

FIGS. 5A-5E illustrate example augmented video frames containing characterization and medical guideline information, consistent with embodiments of the present disclosure. The augmented frames illustrated in FIGS. 5A-5E may be displayed in real-time during capture of the video (e.g., during a medical examination), as discussed above. While polyps are illustrated in the example frames of FIGS. 5A-5E, it is to be understood that the disclosed embodiments may be used with any other object of interest. As shown in FIGS. 5A-5E, the frames may include characterization information associated with one or more features, such as classification, size, and/or location of a polyp. For example, as shown in FIG. 5A, a polyp may be classified as a non-adenoma, and a corresponding representation such as "non-ade" may be displayed; or, as shown in FIGS. 5B and 5C, the polyp may be classified as an adenoma, and a corresponding representation such as "ade" may be displayed. Likewise, as shown in FIGS. 5A and 5C, a polyp may be determined to have a diminutive size, and a corresponding representation such as "dim" may be displayed; or, as shown in FIG. 5B, the polyp may be determined to have a non-diminutive size, and a corresponding representation such as "non-dim" may be displayed. Similarly, as shown in FIGS. 5A-5D, the body location of a polyp may be determined and a corresponding representation may be displayed, such as "Rectum" (FIG. 5A), "Ascending" (FIG. 5B), "Caecum" (FIG. 5C), and "Sigma—rectum" (FIG. 5D). If the location cannot be determined, then no location information may be displayed with the augmented frame. Other representations may be used, consistent with the present disclosure, such as one or more images, icons, videos, shapes, or numbers.

Figure 5E:
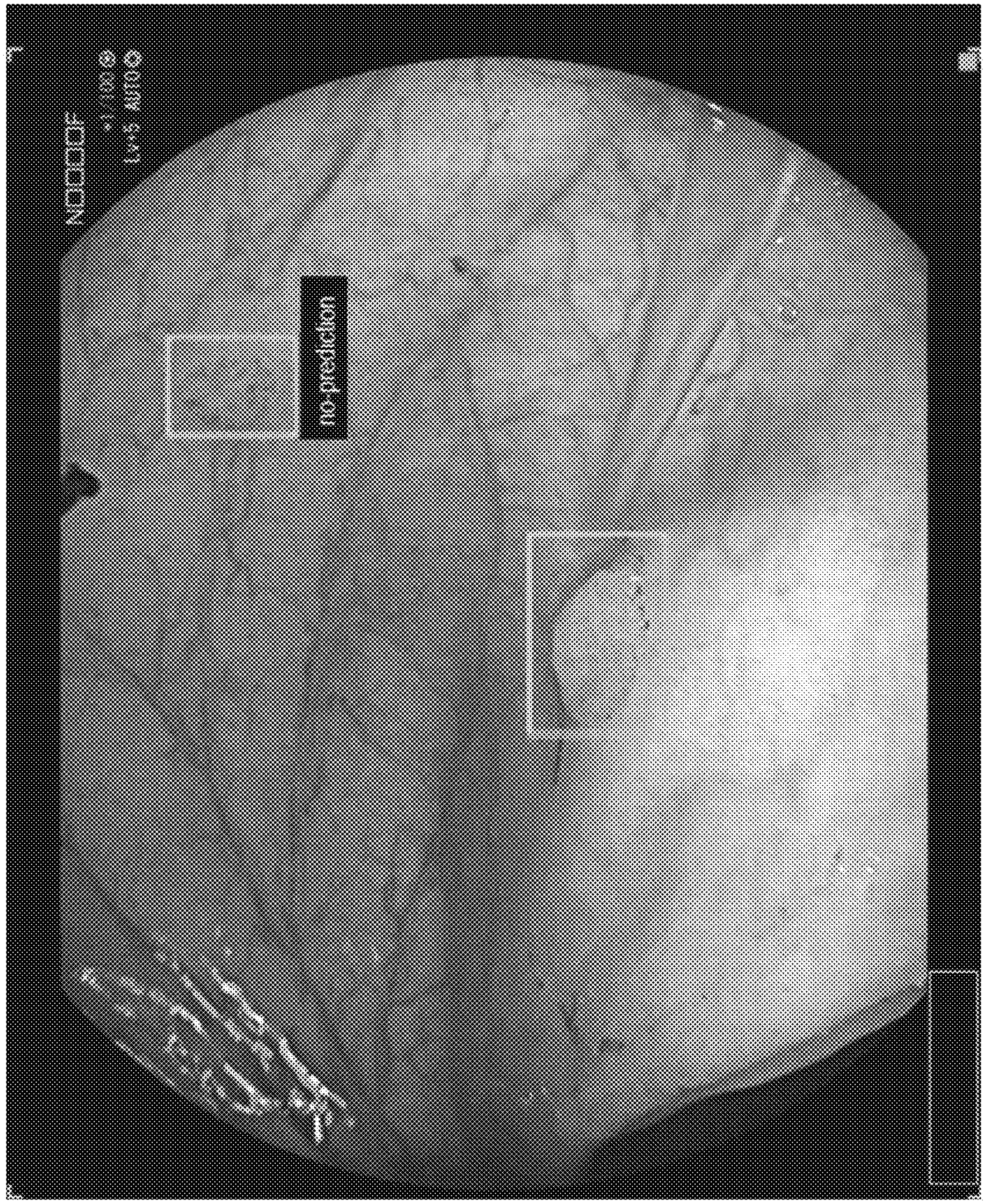

Furthermore, as discussed above, a medical guideline may also be displayed. As shown in FIG. 5A, for example, the medical guideline based on the classification, size, and/or location may be to not remove the polyp, and a corresponding representation such as "leave" may be displayed. As shown in FIGS. 5B and 5C, however, the medical guide may be to remove the polyp (or to perform any other procedure or treatment), and a corresponding representation such as "resect" may be displayed. Moreover, characterization and medical guideline information may be displayed (and determined) independently for each polyp in a plurality of polyps in the frames. As shown in FIG. 5C, for example, separate classification and size information may be displayed adjacent to each detected polyp, which may be different depending on the context. Additionally, other information other than characterization and medical guideline information may be displayed. For example, as shown in FIGS. 5D and 5E, a state of the characterization network and/or the computing device may be displayed, such as whether the characterization network and/or the computing device is currently "analyzing" the frames (FIG. 5D), there is "no prediction" (FIG. 5E), or there is no characterization yet (shown as a blank field for the object detected in the middle of the frame in FIG. 5E). Examples of other information that may be displayed include the characterization network and/or the computing device partially characterizing the polyp, a confidence value being too low, an error having occurred, the system restarting, a user action or input, or any other information associated with the processing of the real-time video.

In some embodiments, additional modules or processes may be provided and performed before, after, or concurrently with characterization network 430. For example, in some embodiments, the at least one processor may be configured to apply one or more neural networks that implement a trained quality network configured to determine a frame quality associated with at least one of the plurality of frames. A "frame quality," as used herein, may refer to a degree of visual clarity of one or more frames for purposes of performing the operations described herein. A frame quality may be based on any visual characteristic, such as blurriness, sharpness, brightness, lighting, exposure, contrast, movement, visibility, or any other feature of one or more frames. The trained frame quality network may be trained to generate a numeric value and/or a quality classification associated with a frame quality. For example, the trained frame quality network may be configured to output a number (e.g., 0.7) associated with the frame quality, or it may be configured to assign a quality class to a frame (e.g., "sufficient quality" or "not sufficient quality").

The trained frame quality network may comprise one or more suitable machine learning networks or algorithms for determining a quality value associated with one or more frames in the real-time video, including one or more neural networks (e.g., a deep neural network, a convolutional neural network, a recursive neural network, etc.), a random forest, a support vector machine, or any other suitable model as described above trained to determine a frame quality. The frame quality network may be trained using a plurality of training frames or portions thereof labeled based on one or more quality values or classifications. For example, a first set of training frames (or portions of frames) may be labeled as "sufficient quality," and a second set of training frames (or portions of frames) may be labeled as "not sufficient quality." Weights or other parameters of the frame quality network may be adjusted based on its output with respect to a third, non-labeled set of training frames (or portions of frames) until a convergence or other metric is achieved, and the process may be repeated with additional training frames (or portions thereof) or with live data as described herein. The trained frame quality network may be stored in the computing device and/or system, or it may be fetched from a network or database prior to determining the frame quality. In some embodiments, the trained frame quality network may be re-trained based on one or more of its outputs, such as accurate or inaccurate frame quality detections. The feedback for re-training may be generated automatically by the system or the computing device, or it may be manually inputted by the operator or another user (e.g., through a mouse or keyboard or other input device). Weights or other parameters of the trained frame quality network may be adjusted based on the feedback. In some embodiments, conventional non-machine learning frame quality detection networks or algorithms may be used, either alone or in combination with the trained frame quality network.

In some embodiments, the trained frame quality network may be configured to generate a confidence value associated with the determined frame quality. A confidence value for a determined frame quality may refer to an indication of the level of certainty associated with the determined frame quality. For example, a confidence value of 0.9 or 90% may indicate that there is a ninety percent certainty that the determined frame quality is correct, while a confidence value of 0.4 or 40% may indicate that there is a forty percent certainty that the determined frame quality is correct, and so forth. Other values, metrics, or representations may be used to represent a confidence value, however. For example, a confidence value may be categorized as "high confidence" when the confidence value is above a predetermined threshold (e.g., above 66% confidence), "low confidence" when the confidence value is below a predetermined threshold (e.g., below 33% confidence), or "undetermined" when between two predetermined thresholds (e.g., 33% to 66% confidence). In some embodiments, the at least one processor may be configured to present, in real-time on the display device, information for the determined frame quality in any suitable format (e.g., the frame quality value and/or classification, a thumbs up or thumbs down, a check mark or cross sign, or a color).

The at least one processor of the computing device or system may be configured to aggregate data associated with a determined characterization (e.g., classification, location, and/or size) when at least one of the determined frame quality or the confidence value is above a predetermined threshold, consistent with the embodiments of the present disclosure. Aggregation in this context may refer to any operation for combining, collecting, or receiving multiple data. For example, in embodiments where the classification, location, and size of an object of interest in a frame are determined, the at least one processor may be configured to collect the classification, location, and size determination from the characterization network only when the determined frame quality from the frame is above the predetermined threshold (e.g., having a frame quality greater than 0.4 or being classified as "sufficient quality"). In some embodiments, the at least one processor may be configured to present, on the display device, at least a portion of the aggregated data. The aggregated data may be displayed in the same or similar manner as described above (e.g., using an LED display, virtual reality display, or augmented reality display).

Other information may be aggregated, such as other determined features, and other metrics may be used to determine whether to aggregate the data depending on the specific application or context. In some embodiments, for example, the at least one processor may be configured to aggregate, when the object of interest persists over more than one of the plurality of frames, information associated with the determined features (e.g., location and size) of the object of interest. A "persistence," or variations thereof as used herein, may refer to an object of interest's continued presence in a location of one or more frames. A persistence may be determined using any process for comparing the presence of an object of interest in one or more frames. For example, an Intersection over Union (IoU) value for the location of an object of interest in two or more image frames may be calculated, and the IoU value may be compared with a threshold to determine whether the object of interest persists over more than one of the frames. An IoU value may be estimated using the following formula:

$$-(IoU) = \frac{AreaofOverlap}{Areaof \bigcup}$$

In the above IoU formula, Area of Overlap is the area where the object of interest is present in two or more frames, and Area of Union is the total area where the object of interest is present in the two or more frames. As a non-limiting example, an IoU value above 0.5 (e.g., approximately 0.6 or 0.7 or higher, such as 0.8 or 0.9) between two consecutive frames may be used to determine that the object of interest persists in the two consecutive frames. In contrast, an IoU value below 0.5 (e.g., approximately 0.4 or lower) between the same may be used to determine that the object of interest does not persist. Other methods of determining a persistence may be used, however, depending on the application or context. When the object is determined to persist over more than a plurality of frames, information associated with the determined features (e.g., location and size) of the object of interest may be aggregated, in the same or similar manner as discussed above. The at least one processor may be configured to present, on a display device, the aggregated data or a portion thereof. In this manner, information may be displayed only for objects of interest that are sufficiently present in two or more frames, so as to avoid displaying useless or distracting information during capture (e.g., during a medical procedure).

In some embodiments, aggregated information may be displayed based on one or more criteria. For example, the at least one processor may be configured to present, on a display device, when the determined location is in a first body region and the determined size is within a first range, the aggregated information (e.g., location and size) for the object of interest. Further, the at least one processor may be configured to present, on the display device, when the determined location is in a second body region and the determined size is within a second range, information indicating a status of the characterization of the object of interest (i.e., non-aggregated information). As a non-limiting example, in embodiments where the object of interest is a polyp and the aggregated information is location and size, classification information (i.e., non-aggregated information) may be displayed when the polyp is determined to be diminutive and located in a body location other than the sigma rectum. Conversely, the location and size (i.e., the aggregated information) may be displayed when the polyp is determined to be non-diminutive or located in the sigma rectum. In this manner, only relevant information may be displayed to an operator based on predetermined aggregation rules and/or display criteria so as to provide only critical information during capture (e.g., during a medical procedure).

Figure 6:
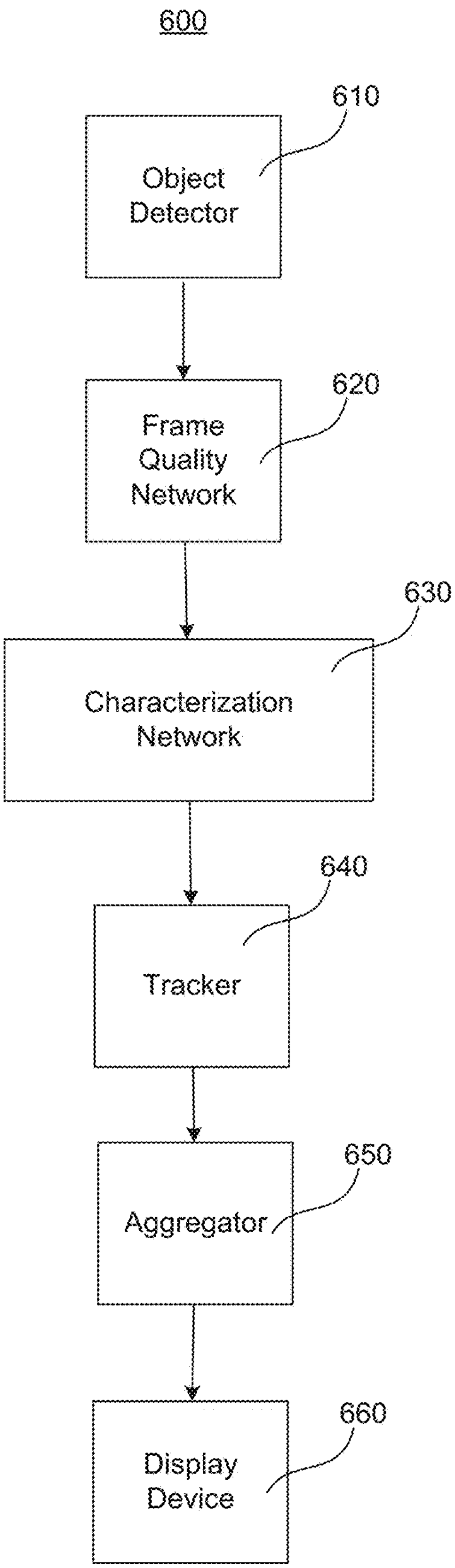
FIG. 6 illustrates another example system for processing real-time video, consistent with embodiments of the present disclosure.

FIG. 6 illustrates another exemplary system 600 for processing real-time video, consistent with disclosed embodiments. As shown in FIG. 6, a real-time processing system 600 may comprise an object detector 610, a frame quality network 620, a characterization network 630, a tracker 640, an aggregator 650, and a display device 660. The components (610, 620, 630, 640, 650) of FIG. 6 may be implemented with computing device(s) or one or more processors. Object detector 610 may be the same or similar as object detector 420 described above in connection with FIG. 4A (e.g., a machine learning detection network of algorithm or a conventional detection algorithm), characterization network 630 may be the same or similar to characterization network 430 discussed above in connection with FIG. 4A (or it may comprise more or less networks), and display device 470 may be the same or similar as the display device 180 described above in connection with FIG. 1 (e.g., an LCD, LED, or OLED display, augmented reality display, or virtual reality display). Comparing FIG. 4A with FIG. 6, it can be seen that additional operations may be performed before, after, or concurrently with characterization network 630. For example, in FIG. 6, frame quality network 620, tracker 640, and aggregator 650 may perform operations at any time with respect to the operations of the characterization network 630. Although arrows are used in FIG. 6 and other figures to denote a general flow of information in some embodiments, it is to be understood that operations may happen in a different order or concurrently with one or more other operations, and other steps may be added or skipped altogether.

In FIG. 6, object detector 610 may detect one or more objects of interest in the plurality of frames and may send its output to frame quality network 620 and/or characterization network 630. In some embodiments, although shown as two separate components, frame quality network 620 may be part of characterization network 630. Frame quality network 620 may be configured to determine a frame quality and/or a confidence value associated with the frame quality for frames containing a detected object of interest, as described above, and send its output to characterization network 630 and/or tracker 640.

In some embodiments, frame quality network 620 may classify frames from an image device and/or patches of frames containing an object of interest detected by object detector 610 based on a set of classes learned in training. Frame quality network 620 may output a confidence value of its output by learning implicitly during training using, for example, one-hot-encoding formulation. Alternatively, a dedicated output node may be added to frame quality network 620 to provide a confidence estimation and an abstention term included in the loss function to train the network. Frame quality network 620 may use the abstention term to predict low confidence values when the estimation error is high due to, for example, low quality or cluttered image frames. In some embodiments, frame quality network 620 may learn to generate confidence values of its output explicitly if a confidence value of a ground truth value is available for the training data used to train frame quality network 620. In some embodiments, frame quality network 620 may use neural network calibration methods such as mixup and label smoothing during training to control the range and distribution of confidence values. One or more neural networks may be used to implement frame quality network 620 and may be trained to predict both the output and a confidence value or label uncertainty, if available.

Characterization network 630 may identify one or more features and/or confidence values associated with the one or more features of the detected object of interest, as discussed above. In embodiments where characterization network 630 receives a frame quality and/or a confidence value associated with the frame quality from frame quality network 620, characterization network 630 may be configured to detect (or provide an output for) features of the object of interest only in frames where the frame quality and/or the confidence value associated with the frame quality are above a predetermined threshold (e.g., greater than 0.4 or classified as "sufficient quality"). Tracker 640 may be configured to determine a persistence of a detected object of interest, as described above. In some embodiments, tracker 640 may receive feature detections from characterization network 630 and may be configured to only provide them as output when it determines that the detected object of interest persists over more than one of the frames or a predetermined number of frames. In some embodiments, tracker 640 may be configured to receive a frame quality and/or a confidence value associated with the frame quality, which it may utilize with its persistence determination to determine whether to provide an output (e.g., it may provide an output only when the detected object of interest persists in more than one of the frames or a predetermined number of frames and the frame quality and/or confidence value are above a predetermined threshold).

Aggregator 650 may receive outputs from any of the previously mentioned components, including object detector 610, frame quality network 620, characterization network 630, and/or tracker 640, and it may aggregate or combine any of the received information based on one or more criteria for presentation on display 660, as discussed above. For example, aggregator 650 may receive information associated with features detected by characterization network 630 to determine what features to aggregate depending on predefined criteria. For example, aggregator 650 may output, to display device 660, when the determined location is in a first body region and the determined size is within a first range, the aggregated location and size information for the object of interest. Additionally, or alternatively, aggregator 650 may output, to display device 660, when the determined location is in a second body region and the determined size is within a second range, information indicating a status of the characterization of the object of interest instead. By way of example, the status of the characterization of the object of interest provided by the aggregator 650 may include the status of the aggregation to inform the operator or user as to whether there is aggregated information or only non-aggregated information. Aggregator 650 may use other rules and criteria to output information for presentation on display device 660, as discussed above.

Figure 7:
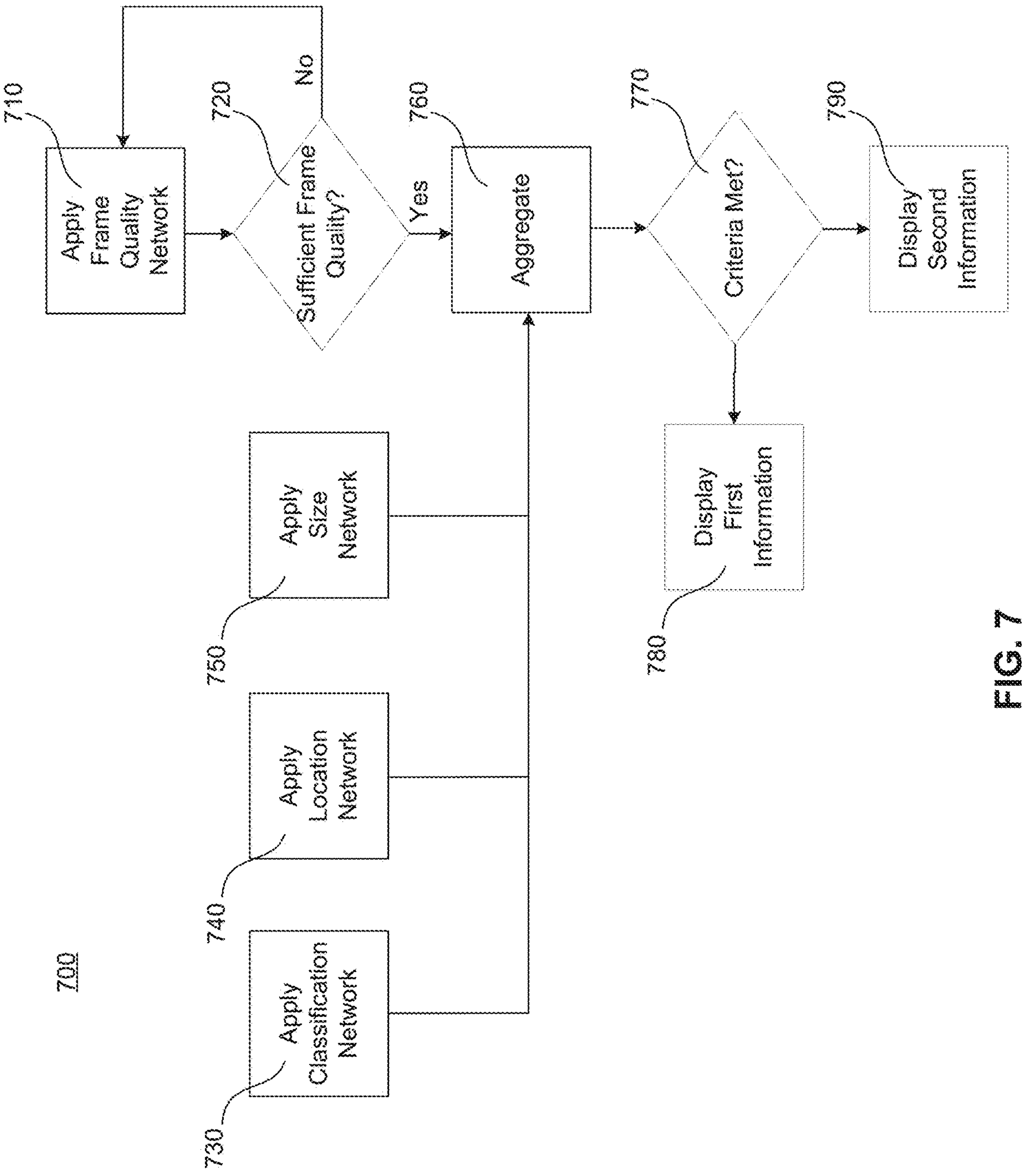
FIG. 7 illustrates a block diagram of an example method for aggregating information for presentation on a display device, consistent with embodiments of the present disclosure.

FIG. 7 illustrates a block diagram of an example method 700 for aggregating information for presentation on a display, consistent with embodiments of the present disclosure. The example method 700 may be implemented with one or more processors. In one embodiment, method 700 is implemented with a computing device or system, such as system 600 of FIG. 6. It will be appreciated that this is a non-limiting example.

As shown in FIG. 7, at step 710 a frame quality network may be applied to a frame containing or not containing an object of interest to determine a frame quality and a confidence value associated with the frame quality, as discussed above. At step 720, the frame quality and the confidence value may be compared to a threshold to determine whether the frame has a sufficient frame quality. If the frame has a sufficient frame quality, then the method proceeds to aggregate data. If the frame does not have sufficient frame quality, then the method returns to step 710 so that another frame can be examined.

At steps 730, 740, and 750, a classification network, a location network, and a size network may be applied to determine a classification, location, and size of the detected object of interest, respectively, as discussed above. At step 760, if the frame has a sufficient frame quality, at least a portion or set of the classification, location, and size information is aggregated. At step 770, one or more criteria is applied to determine what portion of the aggregated data to present for display (e.g., whether the determined location is in a first body region and the determined size is within a first range, or whether determined location is in a second body region and the determined size is within a second range), as discussed above. If a first set of criteria are met, then at step 780 a first portion of the aggregated information may be displayed. If a second set of criteria are met, then at step 790 a second portion of the aggregated information may be displayed. Although not shown in FIG. 7, there may be additional criteria or combinations of criteria applied at step 770 to determine whether or not to display information as part of an augmented display.

Figure 8:
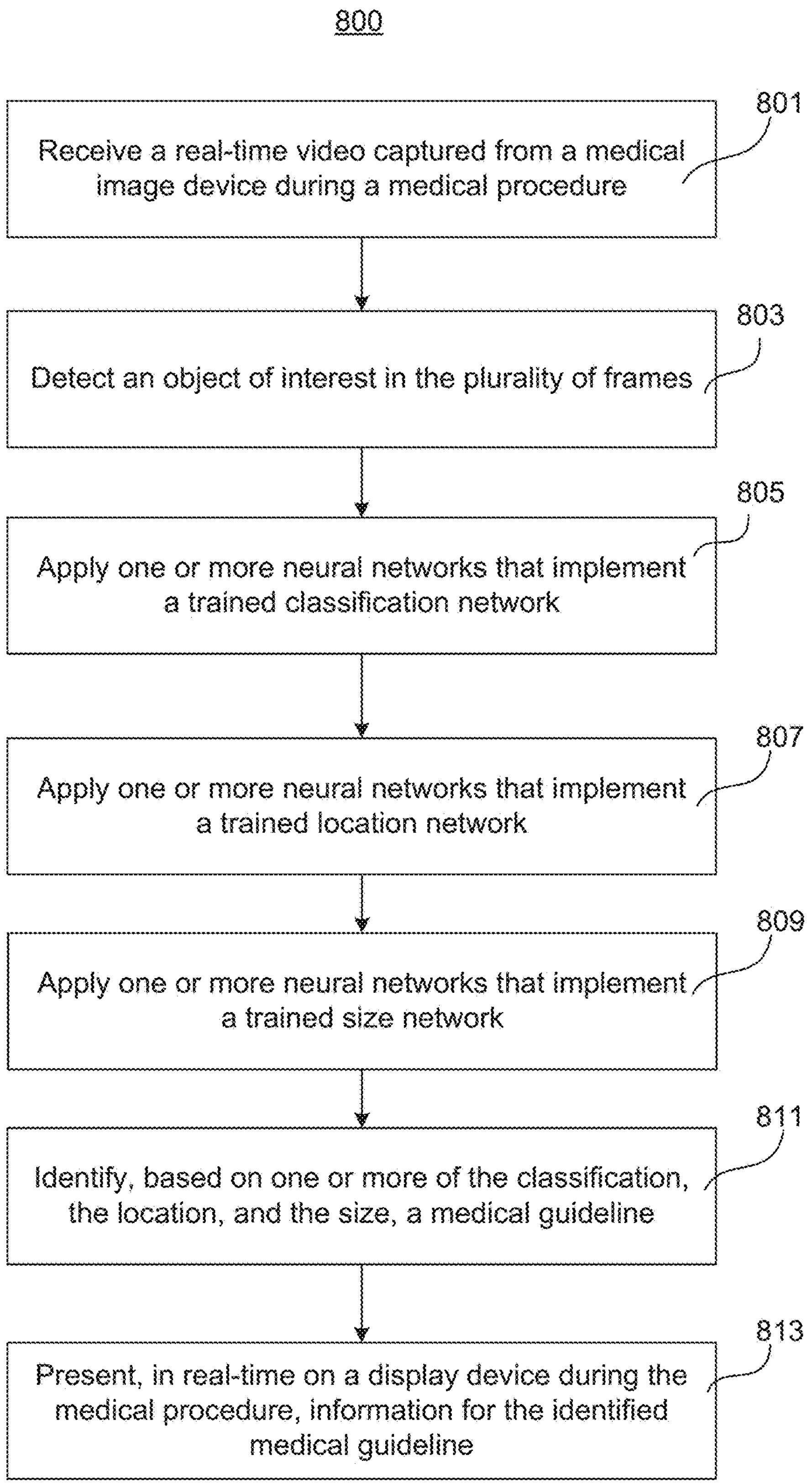
FIG. 8 illustrates a block diagram of an example method for processing real-time video, consistent with embodiments of the present disclosure.

FIG. 8 illustrates a block diagram of an example method 800 for processing real-time video, consistent with embodiments of the present disclosure. The example method 800 may be implemented with computing device(s) or one or more processors. In one embodiment, method 800 is implemented with a computing device or system, such as system 100 of FIG. 1 or system 400 or FIG. 4A. It will be appreciated that these are non-limiting examples.

FIG. 8 includes steps 801 to 813. At step 801, at least one processor may receive a real-time video captured from a medical image device during a medical procedure, the real-time video comprising a plurality of frames, as discussed above. At step 803, the at least one processor may detect an object of interest in the plurality of frames, as discussed above. At block 805, the at least one processor may apply one or more neural networks that implement a trained classification network configured to determine a classification of the object of interest, as discussed above. At block 807, the at least one processor may apply one or more neural networks that implement a trained location network configured to determine a location associated with the object of interest, as discussed above. At block 809, the at least one processor may apply one or more neural networks that implement a trained size network configured to determine a size associated with the object of interest, as discussed above. At block 811, the at least one processor may identify, based on one or more of the classification, the location, and the size, a medical guideline, as discussed above. At block 813, the at least one processor may present, in real-time on a display device during the medical procedure, information for the identified medical guideline, as discussed above.

The diagrams and components in the figures described above illustrate the architecture, functionality, and operation of possible implementations of systems, methods, and computer hardware or software products according to various example embodiments of the present disclosure. For example, each block in a flowchart or diagram may represent a module, segment, or portion of code, which includes one or more executable instructions for implementing the specified logical functions. It should also be understood that in some alternative implementations, functions indicated in a block may occur out of order noted in the figures. By way of example, two blocks shown in succession may be executed or implemented substantially concurrently, or two blocks may sometimes be executed in reverse order, depending upon the functionality involved. Furthermore, some blocks may also be omitted. It should also be understood that each block of the diagrams, and combination of the blocks, may be implemented by special purpose hardware-based systems that perform the specified functions or acts, or by combinations of special purpose hardware and computer instructions. Computer program products (e.g., software or program instructions) may also be implemented based on the described embodiments and illustrated examples.

It should be appreciated that the above-described systems and methods may be varied in many ways, including omitting or adding steps, changing the order of steps and the type of functions and/or components used. It should also be appreciated that different features may be combined in different ways. In particular, not all the features shown above in a particular embodiment or implementation are necessary in every embodiment or implementation. Further combinations of the above features and implementations are also considered to be within the scope of the herein disclosed embodiments or implementations.

While certain embodiments and features of implementations have been described and illustrated herein, modifications, substitutions, changes and equivalents will be apparent to those skilled in the art. It is, therefore, to be understood that the appended claims are intended to cover all such modifications and changes that fall within the scope of the disclosed embodiments and features of the illustrated implementations. It should also be understood that the herein described embodiments have been presented by way of example only, not limitation, and various changes in form and details may be made. Any portion of the systems and/or methods described herein may be implemented in any combination, except mutually exclusive combinations. By way of example, the implementations described herein can include various combinations and/or sub-combinations of the functions, components and/or features of the different embodiments described.

Moreover, while illustrative embodiments have been described herein, the scope of the present disclosure includes any and all embodiments having equivalent elements, modifications, omissions, combinations (e.g., of aspects across various embodiments), adaptations or alterations based on the embodiments disclosed herein. Further, elements in the claims are to be interpreted broadly based on the language employed in the claims and not limited to examples described herein or during the prosecution of the present application. Instead, these examples are to be construed as non-exclusive. Further, the steps of the disclosed methods can be modified in any manner, including by reordering steps or inserting or deleting steps.

By way of further example, systems and methods consistent with the present disclosure include the following implementations and aspects.

A computer-implemented system for processing real-time video, the system comprising at least one processor configured to: receive a real-time video captured from a medical image device during a medical procedure, the real-time video comprising a plurality of frames; detect an object of interest in the plurality of frames; encode the object of interest in the plurality of frames to generate an embedded representation using an encoder network processing an area surrounding the object of interest; generate a latent representation of the encoded object of interest; apply one or more neural networks that implement a trained characterization network to the latent representation to determine one or more characteristics of the object of interest; modify the real-time video with augmenting information of the detected object of interest and the one or more characteristics of the object of interest; and present the modified video on a display device during the medical procedure.

In the above-described system, the medical procedure may include at least one of an endoscopy, a gastroscopy, a colonoscopy, or an enteroscopy. Further, the object of interest may include at least one of a formation on or of human tissue, a change in human tissue from one type of cell to another type of cell, an absence of human tissue from a location where the human tissue is expected, or a lesion.

In the above-described system, the at least one processor may be further configured to identify, based on the one or more characteristics of the object of interest, a medical guideline. The at least one processor may also be configured to present information related to the identified medical guideline as part of the modified video on the display device. By way of example, the information related to the identified medical guideline may include an instruction to leave or resect the object of interest. As a further example, the information related to the identified medical guideline includes a type of resection.

In the above-described system, the at least one processor may be further configured to generate a confidence value associated with the identified medical guideline.

In the above-described system, the determined one or more characteristics of the object of interest may include a classification of the object interest based on at least one of a histological classification, a morphological classification, a structural classification, or a malignancy classification. As a further example, the determined one or more characteristics of the object of interest may include a location associated with the object of interest. In some embodiments, the determined location is a location in a human body or relative to a human organ. Examples of a determined location includes a rectum, sigmoid colon, descending colon, transverse colon, ascending colon, or cecum. As a still further example, the determined one or more characteristics of the object of interest may be a size of the object of interest. The determined size of the object of interest may be represented as a numeric value or a size classification.

In the above-described system, the at least one processor may be further configured to apply one or more neural networks that implement a trained quality network. The trained quality network may be configured to: determine a frame quality associated with one or more of the plurality of frames; and generate a confidence value associated with the determined frame quality.

In the above-described system, the at least one processor may be further configured to: aggregate data associated with the determined one or more characteristics when at least one of the determined frame quality or the confidence value is above a predetermined threshold; and present, on the display device, at least a portion of the aggregated data.

In the above-described system, the at least one processor may be further configured to: detect a plurality of objects of interest in the plurality of frames; determine a plurality of classifications and sizes associated with the plurality of detected objects of interest; and present, on the display device, information associated with one or more determined classifications and sizes.

In the above-described system, the at least one processor may be further configured to track the object of interest in the plurality of frames to determine temporal information related to the object of interest.

A computer-implemented method for processing real-time video, the method comprising the following steps: receiving a real-time video captured from a medical image device during a medical procedure, the real-time video comprising a plurality of frames; detecting an object of interest in the plurality of frames; encoding the object of interest in the plurality of frames to generate an embedded representation using an encoder network processing an area surrounding the object of interest; generating a latent representation of the encoded object of interest; applying one or more neural networks that implement a trained characterization network to the latent representation to determine one or more characteristics of the object of interest; modifying the real-time video with augmenting information of the detected object of interest and the one or more characteristics of the object of interest; and presenting the modified video in real-time on a display device during the medical procedure.

A computer-implemented system for processing real-time video, the system comprising at least one processor configured to: receive a real-time video captured from a medical image device during a medical procedure, the real-time video comprising a plurality of frames; detect an object of interest in the plurality of frames; encode the object of interest in the plurality of frames to generate an embedded representation using an encoder network processing an area surrounding the object of interest; generate a latent representation of the encoded object of interest; track, based on the latent representation, the object of interest in the plurality of frames to determine temporal information of the object of interest; and apply one or more neural networks that implement a trained characterization network to determine one or more characteristics of the object of interest, wherein the one or more characteristics are determined based on at least one of the latent representation and temporal information.

In the above described system, the at least one processor may be further configured to: modify the real-time video with augmenting information of the detected object of interest and the one or more characteristics of the object of interest; and present the modified video on a display device during the medical procedure. The medical procedure may include at least one of an endoscopy, a gastroscopy, a colonoscopy, or an enteroscopy. Further, the object of interest may include at least one of a formation on or of human tissue, a change in human tissue from one type of cell to another type of cell, an absence of human tissue from a location where the human tissue is expected, or a lesion.

In the above-described system, the at least one processor may be further configured to identify, based on the one or more characteristics of the object of interest, a medical guideline. The at least one processor may also be configured to present information related to the identified medical guideline as part of the modified video on the display device. By way of example, the information related to the identified medical guideline may include an instruction to leave or resect the object of interest. As a further example, the information related to the identified medical guideline includes a type of resection.

In the above-described system, the at least one processor may be further configured to generate a confidence value associated with the identified medical guideline.

In the above-described system, the determined one or more characteristics of the object of interest may include a classification of the object interest based on at least one of a histological classification, a morphological classification, a structural classification, or a malignancy classification. As a further example, the determined one or more characteristics of the object of interest may include a location associated with the object of interest. In some embodiments, the determined location is a location in a human body or relative to a human organ. Examples of a determined location includes a rectum, sigmoid colon, descending colon, transverse colon, ascending colon, or cecum. As a still further example, the determined one or more characteristics of the object of interest may be a size of the object of interest. The determined size of the object of interest may be represented as a numeric value or a size classification.

In the above-described system, the at least one processor may be further configured to apply one or more neural networks that implement a trained quality network. The trained quality network may be configured to: determine a frame quality associated with one or more of the plurality of frames; and generate a confidence value associated with the determined frame quality.

In the above-described system, the at least one processor may be further configured to: aggregate data associated with the determined one or more characteristics when at least one of the determined frame quality or the confidence value is above a predetermined threshold; and present, on the display device, at least a portion of the aggregated data.

In the above-described system, the at least one processor may be further configured to: detect a plurality of objects of interest in the plurality of frames; determine a plurality of classifications and sizes associated with the plurality of detected objects of interest; and present, on the display device, information associated with one or more determined classifications and sizes.

In the above-described system, the at least one processor may be further configured to track the object of interest in the plurality of frames to determine temporal information related to the object of interest. To track the object of interest, the at least one processor may be configured to track the object of interest in the plurality of frames based on similarity of latent representations of the object of interest in the plurality of frames. Additionally, or alternatively, to track the object of interest, the at least one processor may be configured to determine the number of frames over which there is a persistence of the object of interest. The at least one processor may also be configured to track the object of interest based on frame quality information for each frame.

A computer-implemented method for processing real-time video, the method comprising: receiving a real-time video captured from a medical image device during a medical procedure, the real-time video comprising a plurality of frames; detecting an object of interest in the plurality of frames; encoding the object of interest in the plurality of frames to generate an embedded representation using an encoder network processing an area surrounding the object of interest; generating a latent representation of the encoded object of interest; tracking, based on the latent representation, the object of interest in the plurality of frames to determine temporal information of the object of interest; and applying one or more neural networks that implement a trained characterization network to determine one or more characteristics of the object of interest, wherein the one or more characteristics are determined based on at least one of the latent representation and temporal information.

In the above described method, the method may be further include: modifying the real-time video with augmenting information of the detected object of interest and the one or more characteristics of the object of interest; and presenting the modified video on a display device during the medical procedure. The medical procedure may include at least one of an endoscopy, a gastroscopy, a colonoscopy, or an enteroscopy. Further, the object of interest may include at least one of a formation on or of human tissue, a change in human tissue from one type of cell to another type of cell, an absence of human tissue from a location where the human tissue is expected, or a lesion.

It is intended, therefore, that the specification and examples herein be considered as exemplary only, with a true scope and spirit being indicated by the following claims and their full scope of equivalents.

What is claimed is:

1. A computer-implemented system for processing real-time video, the system comprising at least one processor configured to:

process real-time video captured from a medical image device during a medical procedure, the real-time video comprising a plurality of frames;

detect an object of interest in the plurality of frames;

execute a plurality of neural networks in parallel, the plurality of neural networks including:

a trained classification network configured to determine a classification of the object of interest;

a trained location network configured to determine a location of the object of interest relative to an anatomical portion of a human organ visible in the real-time video; and a trained size network configured to determine a size associated with the object of interest;

identify, based on two or more of the classification, the location, and the size, a medical treatment guideline; and display, in real-time on a display device during the medical procedure, information indicating the identified medical treatment guideline.

2. The system of claim 1, wherein the medical procedure includes at least one of an endoscopy, a gastroscopy, a colonoscopy, or an enteroscopy.

3. The system of claim 1, wherein the object of interest includes at least one of a formation on or of human tissue, a change in human tissue from one type of cell to another type of cell, an absence of human tissue from a location where the human tissue is expected, or a lesion.

4. The system of claim 1, wherein the information indicating the identified medical treatment guideline includes an instruction to leave the object of interest.

5. The system of claim 1, wherein the information indicating the identified medical treatment guideline includes an instruction to resect the object of interest and a type of resection.

6. The system of claim 1, wherein the at least one processor is further configured to generate a confidence value for the identified medical treatment guideline.

7. The system of claim 1, wherein the determined classification is based on at least one of a histological classification, a morphological classification, a structural classification, or a malignancy classification.

8. The system of claim 1, wherein the location in the human organ is one of a location in a rectum, sigmoid colon, descending colon, transverse colon, ascending colon, or cecum.

9. The system of claim 1, wherein the determined size associated with the object of interest is a numeric value or a size classification.

10. The system of claim 1, wherein the at least one processor is further configured to:
- apply one or more neural networks that implement a trained quality network configured to:
  - determine a frame quality associated with at least one of the plurality of frames; and
  - generate a confidence value associated with the determined frame quality.

11. The system of claim 10, wherein the at least one processor is further configured to:
- aggregate data associated with the determined classification, location, and size when at least one of the determined frame quality or the confidence value is above a predetermined threshold; and
- display, on the display device, at least a portion of the aggregated data.

12. The system of claim 1, wherein the at least one processor is further configured to:
- detect a plurality of objects of interest in the plurality of frames;
- determine a plurality of classifications and sizes associated with the plurality of objects of interest, wherein a classification and a size in the plurality of determined classifications and sizes are associated with a detected object of interest in the detected plurality of objects of interest; and
- display, on the display device, information associated with one or more determined classifications and sizes.

13. The system of claim 1, wherein the at least one processor is further configured to:
- apply one or more neural networks that implement an encoder network configured to encode the object of interest in the plurality of frames by processing an area surrounding the object of interest.

14. The system of claim 13, wherein the at least one processor is further configured to:
- generate a latent representation of the object of interest encoded by the encoder network.

15. The system of claim 14, wherein the at least one processor is further configured to:
- provide the latent representation of the object of interest with the classification network, the location network, and the size network.

16. The system of claim 14, wherein the at least one processor is further configured to:
- track the object of interest in the plurality of images to determine temporal information of the object of interest.

17. The system of claim 1, wherein the medical treatment guideline is determined by a characterization network.

18. The system of claim 1, wherein the trained location network is configured to identify the anatomical portion of the human organ from the real-time video and determine the location of the object of interest relative to the identified anatomical portion.

19. A computer-implemented system for processing real-time video, the system comprising at least one processor configured to:
- process real-time video comprising a plurality of frames collected during a medical procedure;
- detect an object of interest in the plurality of frames;
- execute one or more neural networks that implement a trained characterization network configured to:
  - determine a plurality of features associated with the object of interest;
  - determine a location of the object of interest relative to an anatomical portion of a human organ visible in the real-time video; and
  - determine confidence values associated with the plurality of features;
- identify, based on one or more of the plurality of features and the confidence values, a medical treatment guideline; and
- display, in real-time on a display device during the medical procedure, information indicating the identified medical treatment guideline.

20. The system of claim 19, wherein the medical procedure includes at least one of an endoscopy, a gastroscopy, a colonoscopy, or an enteroscopy.

21. The system of claim 19, wherein the object of interest includes at least one of a formation on or of human tissue, a change in human tissue from one type of cell to another type of cell, an absence of human tissue from a location where the human tissue is expected, or a lesion.

22. The system of claim 19, wherein the information indicating the medical treatment guideline includes an instruction to leave the object of interest.

23. The system of claim 19, wherein the information indicating the identified medical treatment guideline includes an instruction to resect the object of interest and a type of resection.

24. The system of claim 19, wherein the at least one processor is further configured to generate a confidence value for the identified medical treatment guideline.

25. The system of claim 19, wherein the trained characterization network comprises:
- a trained classification network configured to determine a classification associated with the object of interest and to generate a classification confidence value associated with the determined classification;
- a trained location network configured to determine a location associated with the object of interest and to generate a location confidence value associated with the determined location; and
- a trained size network configured to determine a size associated with the object of interest and to generate a size confidence value associated with the determined size.

26. The system of claim 18, wherein the at least one processor is further configured to:
- apply one or more neural networks that implement a trained quality network configured to:
  - determine a frame quality associated with at least one of the plurality of frames; and generate a confidence value associated with the determined frame quality.

27. The system of claim 26, wherein the at least one processor is further configured to:

aggregate data associated with the plurality of features when at least one of the determined frame quality or the confidence value is above a predetermined threshold; and display, on the display device, at least a portion of the aggregated data.

28. The system of claim 19, wherein the at least one processor is further configured to:

detect a plurality of objects of interest in the plurality of frames;

determine a plurality of sets of features associated with the plurality of objects of interest, wherein a set of features in the plurality of sets of features includes characterization and size information associated with a detected object of interest in the plurality of objects of interest; and display, on the display device, information associated with one or more sets of features in the plurality of sets of features.

29. A computer-implemented method for processing real-time video, the method comprising:

processing real-time video captured from a medical image device during a medical procedure, the real-time video comprising a plurality of frames;

detecting an object of interest in the plurality of frames;

executing a plurality of neural networks in parallel, the plurality of neural networks including:

a trained classification network configured to determine a classification of the object of interest;

a trained location network configured to determine a location of the object of interest relative to an anatomical portion of a human organ visible in the real-time video; and a trained size network configured to determine a size associated with the object of interest;

identifying, based on two or more of the classification, the location, and the size associated with the object of interest, a medical treatment guideline; and displaying, in real-time on a display device during the medical procedure, information indicating the identified medical treatment guideline.

* * * * *